United States Patent
Zhang et al.

(10) Patent No.: US 11,540,730 B2
(45) Date of Patent: Jan. 3, 2023

(54) DRY ELECTRODE AND PHYSIOLOGICAL MULTI-PARAMETER MONITORING EQUIPMENT

(71) Applicants: SHENZHEN YASUN TECHNOLOGY COMPANY LIMITED, Guangdong (CN); Graduate School at Shenzhen, Tsinghua University, Guangdong (CN)

(72) Inventors: Yue Zhang, Guangdong (CN); Zhuolun Li, Guangdong (CN); Daizong Yang, Guangdong (CN); Bo Wu, Guangdong (CN); Tuo Zhang, Guangdong (CN); Xiafei Lei, Guangdong (CN)

(73) Assignees: SHENZHEN YASUN TECHNOLOGY COMPANY LIMITED, Guangdong (CN); Graduate School at Shenzhen, Tsinghua University, Guangdong (CN)

( * ) Notice: Subject to any disclaimer, the term of this patent is extended or adjusted under 35 U.S.C. 154(b) by 954 days.

(21) Appl. No.: 16/364,171

(22) Filed: Mar. 25, 2019

(65) Prior Publication Data
US 2019/0290137 A1    Sep. 26, 2019

Related U.S. Application Data

(63) Continuation-in-part of application No. PCT/CN2017/101439, filed on Sep. 12, 2017.

(30) Foreign Application Priority Data

Sep. 26, 2016 (CN) .......................... 201621082019.6

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0006* (2013.01); *A61B 5/01* (2013.01);
(Continued)

(58) Field of Classification Search
CPC ..... A61B 5/02055; A61B 5/0006; A61B 5/01; A61B 5/14517; A61B 5/14532;
(Continued)

(56) References Cited

U.S. PATENT DOCUMENTS

2014/0343392 A1* 11/2014 Yang .................... A61B 5/7221
600/393
2015/0073252 A1* 3/2015 Mazar .................. A61B 5/0809
600/391
(Continued)

FOREIGN PATENT DOCUMENTS

CN       2822514 Y    10/2006
CN     101986115 A     3/2011
(Continued)

*Primary Examiner* — Tanmay K Shah
(74) *Attorney, Agent, or Firm* — Winston Hsu

(57) ABSTRACT

A dry electrode and a physiological multi-parameter monitoring equipment are disclosed. The waterproof dry electrode comprises an encapsulation, extraction electrode and a contact surface layer, wherein the extraction electrode and the contact surface layer are connected with each other and disposed in the encapsulation; the contact surface layer comprises an exposed part and an embedded part encapsulation; the encapsulation comprises flexible silica gel and hard plastic portion, the embedded part being embedded into the hard plastic portion, and the hard plastic portion being packaged in the flexible silica gel. Through the above arrangement in the present invention, the dry electrode can reach a waterproof grade of IPX7, which is higher than living waterproof grade of an ordinary dry electrode. The PMPME can be a patch-type acquisition and monitoring equipment which is convenient for long time wearing and
(Continued)

physiological multi-parameter monitoring, with excellent sealing and waterproofness, and the electrode is reusable.

19 Claims, 14 Drawing Sheets

(51) Int. Cl.
| | |
|---|---|
| *A61B 5/01* | (2006.01) |
| *A61B 5/145* | (2006.01) |
| *A61B 5/1455* | (2006.01) |
| *A61B 5/24* | (2021.01) |
| *A61B 5/25* | (2021.01) |
| *A61B 5/259* | (2021.01) |
| *A61B 5/291* | (2021.01) |
| *A61B 5/296* | (2021.01) |
| *A61B 5/389* | (2021.01) |
| *A61B 5/265* | (2021.01) |
| *A61B 5/28* | (2021.01) |
| *A61B 5/021* | (2006.01) |

(52) U.S. Cl.
CPC ...... *A61B 5/14517* (2013.01); *A61B 5/14532* (2013.01); *A61B 5/14552* (2013.01); *A61B 5/24* (2021.01); *A61B 5/25* (2021.01); *A61B 5/259* (2021.01); *A61B 5/265* (2021.01); *A61B 5/28* (2021.01); *A61B 5/291* (2021.01); *A61B 5/296* (2021.01); *A61B 5/389* (2021.01); *A61B 5/445* (2013.01); *A61B 5/746* (2013.01); *A61B 5/02141* (2013.01); *A61B 5/68335* (2017.08); *A61B 5/742* (2013.01); *A61B 5/7405* (2013.01); *A61B 5/7455* (2013.01); *A61B 2560/0214* (2013.01); *A61B 2560/0252* (2013.01); *A61B 2560/0257* (2013.01); *A61B 2560/0475* (2013.01); *A61B 2562/0215* (2017.08); *A61B 2562/0271* (2013.01); *A61B 2562/125* (2013.01); *A61B 2562/16* (2013.01); *A61B 2562/222* (2013.01)

(58) Field of Classification Search
CPC ......... A61B 5/14552; A61B 5/24; A61B 5/25; A61B 5/259; A61B 5/291; A61B 5/296; A61B 5/389; A61B 5/445; A61B 5/746; A61B 5/02141; A61B 5/68335; A61B 5/7405; A61B 5/742; A61B 5/7455; A61B 2560/0214; A61B 2560/0252; A61B 2560/0257; A61B 2560/0475; A61B 2562/0215; A61B 2562/0271; A61B 2562/125; A61B 2562/222; A61B 5/6833; A61B 2562/0209
USPC ....................................................... 600/372
See application file for complete search history.

(56) References Cited

U.S. PATENT DOCUMENTS

| | | | |
|---|---|---|---|
| 2016/0029906 A1 | | 2/2016 | Tompkins |
| 2017/0172961 A1* | | 6/2017 | Heller ................. A61M 11/006 |

FOREIGN PATENT DOCUMENTS

| | | |
|---|---|---|
| CN | 202515658 U | 11/2012 |
| CN | 204246122 U | 4/2015 |
| CN | 104622445 A | 5/2015 |
| CN | 204520680 U | 8/2015 |
| CN | 104997503 A | 10/2015 |
| CN | 205181340 U | 4/2016 |
| CN | 205433651 U | 8/2016 |
| CN | 205493818 U | 8/2016 |
| CN | 106333661 A | 1/2017 |
| CN | 106859628 A | 6/2017 |
| CN | 206333895 U | 7/2017 |
| JP | 2012-183082 A | 9/2012 |

* cited by examiner

DRY ELECTRODE AND PHYSIOLOGICAL MULTI-PARAMETER MONITORING EQUIPMENT

CROSS REFERENCE TO RELATED APPLICATION

This application is a continuation in part application of PCT/CN2017/101439, filed on Sep. 12, 2017, which claims priority from China patent application CN201621082019.6 filed on Sep. 26, 2016. The contents of PCT/CN2017/101439 are all hereby incorporated by reference.

BACKGROUND OF THE INVENTION

1. Field of the Invention

The present invention relates to the field of medical equipment, in particular to a dry electrode and a physiological multi-parameter monitoring equipment.

2. Description of the Prior Art

The electrode slice is mainly applied to monitoring equipment for acquiring physiological electrical signals of a human body, especially for acquiring electrocardiogram (ECG) signals by an electrocardiograph, ECG monitoring equipment, etc. With the rising of the wearable ECG monitoring equipment, the electrode patch has been widely used.

Heart disease is an important cause of death. About one third of the world's death population dies of heart disease every year, and hundreds of thousands of people die of heart disease every year in China. At present, China faces severe problems with its growing aging population, and heart disease has become the major killer among cardiovascular and cerebrovascular diseases that threaten the health of the elderly. On the other hand, since the fast pace of life and the pressure is great in modern society, patients with cardiovascular diseases tend to be younger. Myocardial infarction and karoshi occur from time to time, and a large number of sub-healthy people also need ECG monitoring. The electrode patch can be applied to two scenarios: one is the large hospital scenario where the patients need to be monitored at any time during hospitalization, and the electrode patch is suitable for the large electrocardiograph; the other is the personal healthcare at home scenario where the family users can be sorted into elderly users and sub-health users, involving the prevention and treatment of cardiovascular diseases, and the electrode patch is mainly used in wearable ECG monitoring equipment for real-time and long-term monitoring of ECG signals. It can be seen that the electrode patch has a broad market prospect.

At present, the disposable conductive gel wet electrode is most commonly used in the ECG monitoring, but the disadvantage is that it is easy to be gradually air-dried over time, and its period of validity is short. Moreover, the gradual air drying of the conductive gel will lead to signal acquisition errors and skin allergy, which is not suitable for long-term monitoring. The dry electrode does not employ the conductive gel, and it is directly contacted to the skin, or an electrode for capacitance coupling to form a path.

Traditional electrocardiograph and ECG monitoring equipment, or electroencephalograph and electroencephalogram (EEG) monitoring equipment are more suitable for acquiring the static ECG or EEG signals. With the development of the Internet of Things and the personal healthcare field, the traditional ECG or EEG monitoring equipment cannot meet the needs of personal and family monitoring which requires the monitoring equipment to be small in size, easy to carry and convenient to use. More importantly, the traditional monitoring equipment cannot achieve stable monitoring under static and even dynamic conditions, while nowadays, the patch physiological multi-parameter monitoring equipment can realize this. However, the patch physiological multi-parameter monitoring equipment is poor in waterproof due to its conductive electrodes exposed by the flexible materials, and it can only achieve living waterproof, and cannot achieve a higher level of waterproofing, which will affect the normal monitoring of equipment.

In addition, when a long-term data acquisition is required, due to the limitation of wireless transmission performance, a long transmission time is required for a large amount of ECG data. During the long-term data acquisition, since the battery life is limited, discontinuity of the acquisition will inevitably occur when the equipment is removed to be charged. For a portable patch-type ECG acquisition product, the diagnoses of many heart diseases are often inaccurate due to the insufficient information acquisition. Therefore, it is necessary to provide a new patch-type ECG acquisition equipment to solve these problems existing in the prior art.

The above technical content of the background art is only used to assist in understanding the concept and technical solutions of the present invention, and it does not necessarily belong to the prior arts of this patent application. In the absence of clear evidence that the above content has been disclosed on the filing date of this patent application, the above background art should not be used to evaluate novelty and inventiveness of this application.

SUMMARY OF THE INVENTION

A major objective of the present invention is to provide a dry electrode and a physiological multi-parameter monitoring equipment, so as to solve the technical problem of poor waterproof performance in the prior art.

Thus, the present invention provides a non-disposable/reusable dry electrode, comprising an encapsulation, extraction electrode and a contact surface layer, wherein the extraction electrode and the contact surface layer are disposed in the encapsulation; the encapsulation comprises a first surface and a second surface, the extraction electrode being exposed on the second surface and connected with the contact surface layer, and a glue layer being disposed on the first surface; the contact surface layer comprises an exposed part and an embedded part, the embedded part being disposed in the encapsulation, and the exposed part being exposed on the first surface; the glue layer is provided with an contact surface hole corresponding to the exposed part in position; and the exposed part is provided with a positioning surface for quick adhesion with the glue layer.

Preferably, the present invention may further have the following technical features:

A material of the contact surface layer is conductive silica gel. Further, a base material of the conductive silica gel is nonpolar silica gel, and a conductive filling material is nickel-coated copper powder, silver powder, conductive graphite or acetylene graphite, i.e., conductive particles such as nickel-coated copper powder and silver powder are uniformly mixed into the nonpolar silica gel, and conductive graphite and acetylene carbon black can also be added.

A surface of the exposed part of the contact surface layer is provided with protruded textures, and a groove is formed between the adjacent textures.

A material of the contact surface layer is metal, and further, it is medical-grade stainless steel, a copper sheet, a nickel strip, iron or manganese steel.

A portion of the extraction electrode located in the encapsulation is connected with the embedded part of the contact surface layer by riveting.

The encapsulation is disposed as a flexible insulating encapsulation, and further, a material of the encapsulation is food-grade silica gel or medical-grade silica gel.

The extraction electrode is vertically disposed on a metal joint on the second surface.

The extraction electrode is an outgoing wire horizontally disposed on the second surface. The extraction electrode is an electrode interface horizontally disposed on the second surface.

The glue layer is a medical-grade double-sided adhesive tape. The contact surface layer is located at a center of the first surface, and the extraction electrode is located at a center or an edge of the second surface.

Compared with the prior art, the present invention has the following beneficial effects: in the present invention, the contact surface layer is exposed on the first surface, the glue layer provided with the contact surface layer is adhered to the human skin, and the glue layer is quickly adhered to the encapsulation through the positioning surface to position the glue layer, so that the glue layer can be quickly and accurately replaced, the dry electrode can be reused, and the skin irritation and damage caused by the traditional wet electrode can be avoided; since the electrode is non-disposable, it can be repeatedly used for a long time to reduce the production cost; while the glue layer can be quickly positioned and replaced through the positioning surface.

In a preferred solution, the encapsulation is a flexible insulating encapsulation which mainly supports the electrode, thus improving the fit with the skin, ensuring the wearing comfort and reducing the noise of acquired signal. The material of the encapsulation has a good insulation performance to avoid the occurrence of interference signals. The full-encapsulation sealing injection molding technology achieves a good waterproof effect.

The contact surface layer is located at a center of the whole encapsulation, and may be made of a medical-grade metal material which has strong corrosion resistance, good electrical conductivity and low contact resistance with the skin, and which can prevent allergic reactions. In addition, the manufacturing process thereof is simple, the raw materials can be easily obtained, and the application is wide.

The contact surface layer may also be made of conductive silica gel. As compared with the ordinary wet electrode, the conductive silica gel has a significantly better electrical performance than the wet electrode, and achieves good electrical conductivity.

The conductive silica gel, which employs nickel-coated copper powder and conductive graphite as conductive filling materials, has good electromagnetic shading effect and oxidation resistance, and strong corrosion resistance under acid and alkali environments, thus increasing the service life of electrode. Meanwhile, the cost of nickel-coated copper powder is low.

The conductive silica gel may be the nonpolar silica gel which is a high-activity adsorption material. It is strongly self-adhesive, and highly stable when being adhered to the skin rather than easy to fall off. It has no toxicity, sensitization or irritation and is safe for use.

A surface of the exposed part of the contact surface layer made of the conductive silica gel is provided with protruded textures, and a groove is formed between the adjacent textures. The protruded textures increase the friction between the contact surface layer and the skin, and also play an advantageous role for perspiration. Especially when the human body takes exercises, the grooves between the protruded textures will be full of sweat, which makes the adhesion between the dry electrode and the skin be tighter and firmer, and the sweat acts as a dielectric to improve the electrical conductivity. If there is no protruded texture, the exposed part of the whole contact surface layer is flat conductive silica gel, and the sweat will accumulate between the exposed part and the skin and cannot be discharged. When the sweat increases, the adhesion tightness between the electrode and the skin will be reduced, which causes the electrode to fall off from the skin.

When the conductive silica gel is used as the electrode material, most of the area in the center of the first surface of the dry electrode is adhered to the skin by the self-adhesive patch of conductive silica gel, and only a small area of the first surface on a periphery of the contact surface layer is adhered to the skin by the double-sided adhesive tape; while the wet electrode is adhered to the skin in a large area by adhesive glue except the conductive gel at the center. Thus, the dry electrode using the conductive silica gel can be repeatedly adhered to the skin for many times, and no damage will be caused to the patient's fine hair and skin when the electrode is removed, thereby reducing the pain.

By using the metal or conductive silica gel as the electrode material, no residue such as conductive gel will be left on the skin when the dry electrode is removed.

The extraction electrode is located at the center or edge of the second surface of the encapsulation. A portion of the extraction electrode exposed on the second surface adopts an RF shading wire, thereby avoiding the external electromagnetic interference and improving the anti-interference capability of the signals.

An electrode interface or an outgoing wire horizontally disposed on the second surface is adopted, and when the extraction electrode is covered by clothes, a junction of the outgoing wire and the second surface does not bend.

In addition, the present invention provides a waterproof dry electrode, comprising an encapsulation, extraction electrode and a contact surface layer, wherein the extraction electrode and the contact surface layer are connected with each other and disposed in the encapsulation; the contact surface layer comprises an exposed part and an embedded part, the exposed part being exposed outside the encapsulation; the encapsulation comprises flexible silica gel and hard plastic portion, the embedded part being embedded into the hard plastic portion, and the hard plastic portion being packaged in the flexible silica gel.

Preferably, the present invention may further have the following technical features:

The contact surface layer comprises a contact surface body and a limiting flange which are integrally formed, the limiting flange protruding from an outer side wall of the contact surface body.

A front surface of the contact surface body is the exposed part; the embedded part comprises the limiting flange and portions of the contact surface body except the front surface; the limiting flange and the portions of the contact surface body except the front surface are embedded into the hard plastic portion, and a waterproof embedding surface is formed at a contact position with the hard plastic portion.

The contact surface body is the exposed part, and the embedded part comprises the limiting flange; the limiting flange is embedded into the hard plastic portion, and a waterproof embedding surface is formed at a contact position with the hard plastic portion.

An overall appearance of the hard plastic portion is matched with an overall appearance of the embedded part to increase a contact area between the flexible silica gel and the hard plastic portion.

The encapsulation comprises a first surface and a second surface, the extraction electrode being exposed on the second surface, a glue layer being disposed on the first surface, and the exposed part being exposed on the first surface; the glue layer is provided with an contact surface hole corresponding to the exposed part in position; and the exposed part is provided with a positioning surface for quick adhesion with the glue layer.

A silver/silver chloride film layer is electroplated on the contact surface layer. A material of the contact surface layer is metal, and further, it is medical-grade stainless steel, a copper sheet, a nickel strip, iron or manganese steel, or ABS original plastic; a portion of the extraction electrode located in the encapsulation is connected with the embedded part of the contact surface layer by riveting, butt-welding, laser spot welding and soldering.

A material of the contact surface layer is conductive silica gel. Further, a base material of the conductive silica gel is nonpolar silica gel, and a conductive filling material is nickel-coated copper powder, silver powder, conductive graphite or acetylene graphite, i.e., conductive particles such as nickel-coated copper powder and silver powder are uniformly mixed into the nonpolar silica gel, and conductive graphite and acetylene carbon black may also be added.

A surface of the exposed part of the contact surface layer is provided with protruded textures, and a groove is formed between the adjacent textures.

A portion of the extraction electrode located in the encapsulation is connected with the embedded part of the contact surface layer by riveting, butt-welding, laser spot welding and soldering.

The extraction electrode is a metal joint vertically disposed on the second surface.

The extraction electrode is an outgoing wire horizontally disposed on the second surface.

The extraction electrode is an electrode interface horizontally disposed on the second surface.

The extraction electrode is an electrode interface horizontally disposed on the first surface.

The glue layer comprises a double-sided adhesive tape or a flexible insulating material; the double-sided adhesive tape comprises a medical double-sided adhesive tape or a non-woven double-sided adhesive tape, and the flexible insulating material comprises nonpolar silica gel;

The contact surface hole is matched with the electrode or the sensor of the signal acquisition equipment in shape and size.

The bottom surface of the glue layer is covered with a conductive medium matched with the contact surface hole in shape and size, the conductive medium being aligned with the contact surface hole and adhered to the glue layer.

The conductive medium comprises solid gel, a metal sheet or conductive silica gel, and the solid gel comprises silica gel.

A surface of the solid gel or the conductive silica gel is provided with protruded textures, and a groove is formed between the adjacent textures Light shading glue and/or a miniature sucker array is disposed around the contact surface hole on the bottom surface of the glue layer.

A rear surface of the glue layer is covered with a first-type release layer, and/or the bottom surface of the glue layer is covered with a second-type release layer; the first-type release layer is a segmented release layer, an easily-torn line and/or a gap line being disposed between the contact surface holes for segmentation.

Edges of the glue layer are provided with gripping ears that are integrated with the glue layer, and the gripping ears are non-adhesive to facilitate detachment of the first-type release layer and the second-type release layer, or to tear off the glue layer from a signal acquisition target and/or the dry electrode.

In addition, the present invention provides a physiological multi-parameter monitoring equipment, comprising a circuit module, a flexible housing, a first electrode and a second electrode, wherein the circuit module is packaged in the housing; the first electrode and the second electrode are exposed on a front surface of the housing to acquire electrocardiogram (ECG) or electroencephalogram (EEG) signals and are connected with the circuit module by wires; the first electrode and the second electrode are any dry electrodes aforementioned for acquiring ECG or EEG signals.

Preferably, the present invention may further have the following technical features:

further comprising an upper cover detachably and sealably mounted on a rear surface of the housing, wherein a battery is disposed in the upper cover, and electrically connected with the circuit module in the housing through the upper cover and correspondingly disposed metal contacts on the housing; and the battery can be taken out from the upper cover for replacement or may be a rechargeable battery.

The upper cover is mounted in a groove disposed on the rear surface of the housing, and the fastened upper cover is tightly pressed on a flexible material of the housing to achieve waterproofness; preferably, the upper cover is screwed into a circular groove disposed at the rear surface of the housing by means of thread matching.

The front surface of the housing is provided with a double-sided adhesive material having a through-hole, wherein a bottom surface of the double-sided adhesive material can be adhered to a signal acquisition target, a rear surface of the double-sided adhesive material is adhered to a signal acquisition equipment, and the signal acquisition target is adhered to the signal acquisition equipment through the double-sided adhesive material; the through-hole comprises a first-type through-hole matched with an electrode of the signal acquisition equipment, and/or a second-type through-hole matched with a sensor of the signal acquisition equipment.

The double-sided adhesive material comprises a double-sided adhesive tape or a flexible insulating material, wherein the double-sided adhesive tape comprises a medical double-sided adhesive tape or a non-woven double-sided adhesive tape, and the flexible insulating material comprises nonpolar silica gel.

The through-hole is matched with the electrode or the sensor of the signal acquisition equipment in shape and size.

The bottom surface of the double-sided adhesive material is covered with a conductive medium matched with the first-type through-hole in shape and size, the conductive medium being aligned with the first-type through-hole and adhered to the double-sided adhesive material.

The conductive medium comprises solid gel, a metal sheet or conductive silica gel, and the solid gel comprises silica gel.

A surface of the solid gel or the conductive silica gel is provided with protruded textures, and a groove is formed between the adjacent textures.

Light shading glue and/or a miniature sucker array is disposed around the second-type through-hole on the bottom surface of the double-sided adhesive material.

The rear surface of the double-sided adhesive material is covered with a first-type release layer, and/or the bottom surface of the double-sided adhesive material is covered with a second-type release layer; the first-type release layer is a segmented release layer, a tear line and/or a gap line are arranged between the through-holes to segment.

Edges of the double-sided adhesive material are provided with gripping ears integrated with the double-sided adhesive material, and the gripping ears are non-sticky and are used to facilitate the extraction of the first-type release layer and the second-type release layer, or to tear the self-adhesive patch off the signal acquisition target and/or signal acquisition equipment.

Compared with the prior art, the present invention has the following beneficial effects:

The invention inserts the contact surface layer in the hard plastic, and then encapsulates the contact surface layer arranged with the hard plastic on the basis above, so that the package and the contact surface layer will be connected more closely than the existing contact surface layer, the combination degree is stronger, which improves the waterproofing. If the contact surface layer is connected directly with flexible silica gel, due to the difference of the respective characteristics of the materials, it is impossible to ensure that the joint surface of flexible silica gel and contact surface layer is connected or tightly bonded. Through the setting of hard plastic, a bridge can be established between the flexible silica gel and the contact surface layer, because both the contact surface layer and the flexible silica gel can have a strong bonding degree with the hard plastic. Therefore, it can solve the problem that the waterproof between the contact surface layer and the encapsulation is not good, and the liquid is easy to permeate from the joint surface. Through the above setting, the dry electrode can reach the waterproof grade of IPX7, which is higher than that living waterproof of the general dry electrode. Further, in order to overcome the above deficiencies of the prior art and equipment, any physiological multi-parameter monitoring equipment aforementioned is a patch-type ECG acquisition equipment, comprising the housing made of a flat flexible material suitable for being adhered to a human skin, and a front surface of the housing is provided with the first electrode and the second electrode for acquiring ECG signals by being adhered to the human skin; the housing is integrally formed with the first electrode and the second electrode through a liquid silica gel injection molding or a solid silica gel compression molding; the circuit module for processing acquired ECG data is sealed in the housing, and is connected with the first electrode and the second electrode.

The Beneficial Effects:

As compared with the ECG acquisition equipment in the prior art, the patch-type ECG acquisition equipment comprises a housing made of flat flexible material and integrally formed with the first electrode and the second electrode through a liquid silica gel injection molding, and a circuit module for processing ECG data is sealed in the housing; further, a detachable upper cover with a battery is adopted, and the upper cover is detachably (e.g., by means of thread matching) and sealably mounted on the rear surface of the housing. According to the integrated design of the electrode and the housing, the electrode and the housing can be conveniently adhered to a human body through a medical double-sided adhesive tape to increase the comfort for the human body, and the patch-type ECG acquisition equipment is also convenient to be carried and used, and meanwhile, the waterproof and sealing performance is greatly improved. The design of the detachable upper cover with a battery enables the acquisition of ECG information to be carried out without waiting for a long time due to the charging of the equipment, and the upper cover can be removed to replace the battery or directly use a standby upper cover having a battery of enough power, thus realizing long-time and continuous ECG monitoring of the human body. On the other hand, since the battery is mounted in the upper cover instead of in the housing, it is unnecessary to dispose an openable battery compartment (when the battery is disposable) and a battery charging port (when the battery is rechargeable) on the housing, thus further improving the sealing and waterproof performance of the housing and the internal circuit module thereof.

More advantages can be obtained in the further preferred solutions. For example, a surface of the housing covered by the upper cover is provided with an external storage card slot, into which an external storage card can be conveniently inserted when the upper cover is opened; the ECG data acquired and processed by the circuit module is stored in the external storage card; and when the upper cover is closed, a good waterproof and sealing protection can be achieved, and the use is convenient and safe. For another example, the front surface of the housing is integrally formed with a temperature sensor through a liquid silica gel injection molding or a solid silica gel compression molding, which can not only detect a body temperature through the temperature sensor, but also have a high waterproof performance. For still another example, an alarm device, such as a vibration motor or a speaker, is introduced into the housing; the alarm device is controlled by the circuit module to alarm, such as making a sound or vibration, if a low battery level or an abnormal heart rate is detected under the set conditions. For instance, the alarm device adopts a vibration motor, and preferably the vibration motor may be disposed in the housing or a position on a wall of the housing corresponding to the first electrode and/or the second electrode; the generated vibration can be effectively conducted to the human skin through the electrode sheet, so that the user can obviously detect the vibration alarm.

In another preferred embodiment, by improving the upper cover or the housing, other electrodes are led out from the upper cover or the housing through a plurality of lead wires, so that the equipment can acquire various multi-lead ECG data; for example, the third to fifth electrodes form five-electrode seven-lead together with the first and second electrodes, or other electrodes may also be configured to form ten-electrode twelve-lead together with the first and second electrodes, and so on. Due to this design, the equipment can be provided with either an upper cover without lead wires and electrodes (adopting a single-lead mode), or an upper cover with lead wires and electrodes (adopting a three-lead, seven-lead, twelve-lead, or frank lead system), so that by replacing with different upper covers, a flexible switching can be realized between a single-lead mode and various multi-lead modes, and the ECG data acquisition and accurate discriminant analysis can be performed according to the actual need.

These and other objectives of the present invention will no doubt become obvious to those of ordinary skill in the art after reading the following detailed description of the preferred embodiment that is illustrated in the various figures and drawings.

DETAILED DESCRIPTION

In order to facilitate the understanding, the accurate definitions of the technical terms that will appear later are given as follows.

Hard plastic: it is hard in texture and can generally refer to engineering plastic, such as ABS plastic, POM plastic, polycarbonate (PC), polyethylene terephthalate (PET), polybutylene terephthalate (PBT) and polyphenylene oxide (PPO). Some with harder texture can be medical-grade general-purpose plastic, such as polystyrene (PS).

The present invention will be further described in detail as follows with reference to the specific embodiments and the drawings. It should be emphasized that the following description is merely exemplary and not intended to limit the scope or applications of the present invention.

The non-limiting and non-exclusive embodiments will be described with reference to the drawings, wherein the same drawing mark represents the same part unless otherwise specified.

Embodiment 1

Figure 17:
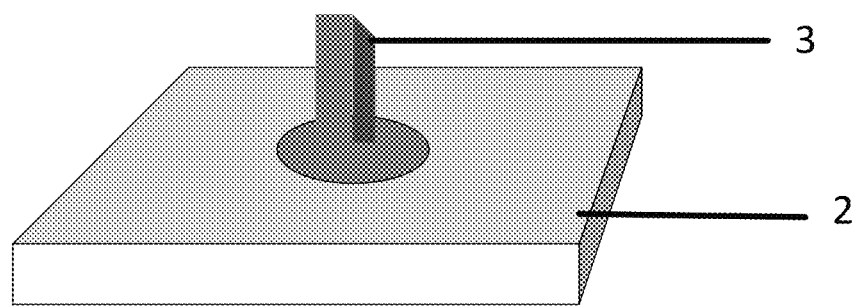
FIG. 17 is a stereo diagram of a non-disposable dry electrode according to an embodiment of the present invention.
Figure 18:
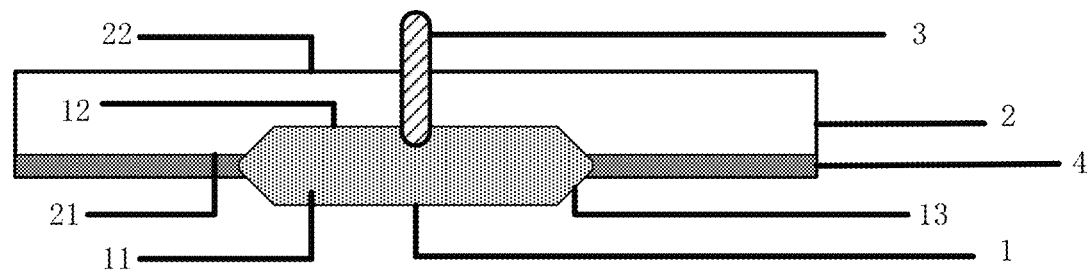
FIG. 18 is a full profile diagram of a non-disposable dry electrode according to an embodiment of the present invention.
Figure 19:
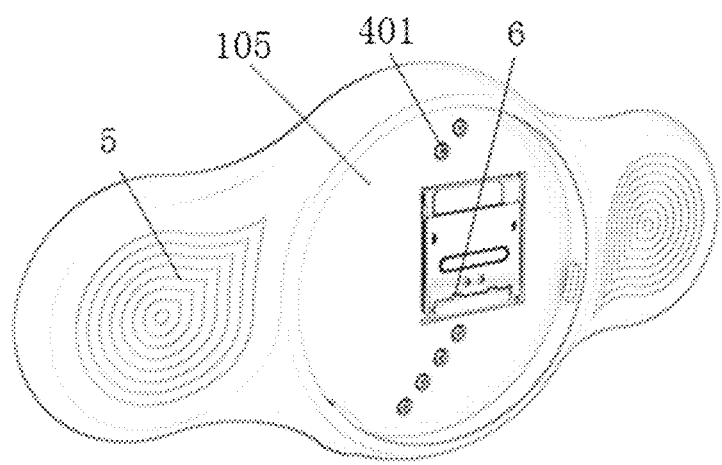
FIG. 19 is a back schematic diagram of a patch-type ECG acquisition equipment according to Embodiment 8 of the present invention without an upper cover.

FIGS. 17-18 illustrate a non-disposable dry electrode, comprising a contact surface layer 1, extraction electrode 3, an encapsulation 2 for wrapping the entire electrode, and a double-sided glue layer 4 adhered to a bottom of the encapsulation; the contact surface layer 1 is exposed on a first surface 21 of the encapsulation 2, the extraction electrode 3 is exposed on a second surface 22 of an upper part of the encapsulation 2, and the extraction electrode 3 is a metal joint vertically disposed on the second surface 22; the extraction electrode 3 and the contact surface layer 1 are connected to each other by riveting, and in some alternative embodiments, the connection mode may also be butt-welding, laser spot welding, soldering, etc.; the double-sided glue layer 4 is directly adhered to the first surface 21 of the encapsulation 2; the contact surface layer 1 comprises an exposed part 11 and an embedded part 12, wherein the embedded part 12 is disposed in the encapsulation 2, and the exposed part 11 is exposed on the first surface 21; the double-sided glue layer 4 is provided with a contact surface hole corresponding to a size and position of the exposed part 11; and the exposed part 11 is provided with a positioning surface 13 for quick adhesion with the double-sided glue layer 4.

The dry electrode embodiment illustrated in FIG. 18 avoids the skin irritation and damage caused by the traditional wet electrode, while it is non-disposable and can be reused for a long time, thereby reducing the production cost and the user's use cost; the encapsulation of the electrode sheet employs the medical-grade flexible silica gel, which improves the fit with the skin and greatly reduces the noise from the signal acquisition. The encapsulation in this embodiment is produced by full-encapsulation sealed silica gel solid-state compression molding or liquid injection molding technology, which can ensure a good waterproof effect.

The contact surface layer 1 is located at the center of the first surface 21 at the bottom of the whole encapsulation. In this embodiment, the material of the contact surface layer 1 is metal, preferably medical-grade stainless steel which has strong corrosion resistance, good electrical conductivity and low contact resistance with the skin, and which can prevent allergic reactions. In addition, the manufacturing process of the medical-grade stainless steel is simple, the raw materials can be easily obtained, and the application is wide. Of course, those skilled in the art can also select other suitable metals according to the actual situation. In order to improve the physiological signal acquisition capability of the contact surface layer, it is preferable to electroplate a silver/silver chloride film layer on the contact surface layer.

The extraction electrode 3 and the metal contact surface layer 1 are connected together by riveting, butt-welding, laser spot welding, soldering or other connection processes, so that the connection is firm and favorable for data transmission.

The encapsulation 2 is composed of a flexible material, which is mainly used for supporting the electrode, and the appropriate pressure provided by the flexible material ensures not only the close fit between the contact surface layer land the human skin, but also the wearing comfort. The material of the encapsulation has a good insulation performance to avoid the occurrence of interference signals. The material of encapsulation 2 is medical-grade soft silica gel to avoid allergic reactions. Of course, those skilled in the art can select other flexible materials according to the actual situation, such as food-grade silica gel, etc.

In the encapsulation 2, the medical-grade solid compression molding or liquid silica gel injection molding technology is adopted to seal a part of the extraction electrode and the metal electrode contact surface by full-encapsulation for waterproof. A silica gel injection is adopted to seal between the extraction electrode 3 and the whole encapsulation 2, so that the waterproof performance is good.

The raw material thickness of the electrode is less than or equal to 0.2 mm, and the overall height is less than 2 to 3 mm, which is 3 mm in this embodiment, so that no foreign body sensation is produced, and the wearing comfort is not affected. The electrode patch needs to fit the chest features, because a too large size will affect the wearing comfort, and a too small size will weaken the effective signal.

In the case where the first surface 21 of the dry electrode is adhered to a human skin using a medical-grade double-sided adhesive tape, only the double-sided adhesive tape needs to be replaced each time, which realizes the repeated use of the dry electrode, reduces the production cost of the dry electrode, and particularly reduces the equipment use cost for users; before each usage, the contact surface layer should be disinfected with medical disinfection alcohol, and the disposing of the positioning surface 13 enables the double-sided glue layer to be quickly adhered.

The outcropping setting of the contact surface layer facilitates the data acquisition on one hand, and facilitates the disposing of the double-sided glue layer on the other hand, thereby realizing the convenience of repeated use.

In this embodiment, the extraction electrode is a metal joint vertically disposed on the second surface. Of course, the extraction electrode may also be an outgoing wire horizontally disposed on the second surface, or an electrode interface horizontally disposed on the second surface, or a motor interface horizontally disposed on the first surface.

Figure 4:
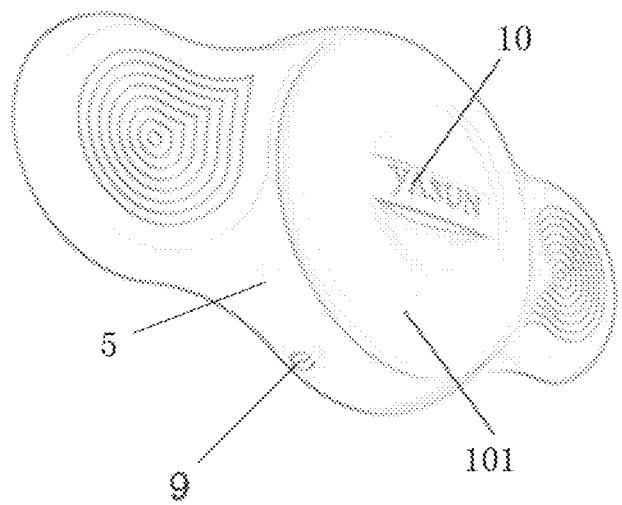
FIG. 4 is a front view of a front surface of a physiological multi-parameter monitoring equipment according to an embodiment of the present invention.
Figure 5:
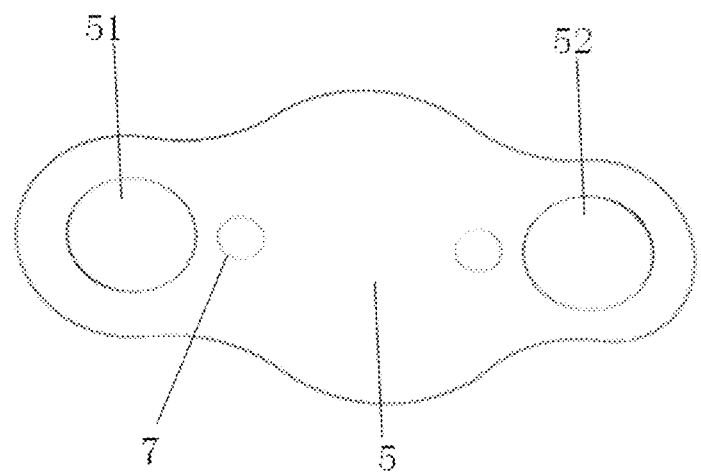
FIG. 5 is a reverse diagram of a rear surface of a physiological multi-parameter monitoring equipment according to an embodiment of the present invention.

In addition, as illustrated in FIGS. 4 to 5, this embodiment further provides a physiological multi-parameter monitoring equipment, comprising a circuit module, a housing 5, and a first electrode 51 and a second electrode 52 exposed on a front surface of the housing to acquire ECG signals, electromyogram (EMG) signals, or EEG signals; the circuit module is packaged in a flexible housing, and the first electrode 51 and the second electrode 52 are connected with the circuit module by wires; the first electrode 51 and the second electrode 52 are any dry electrodes as described above. In this embodiment, the characteristics of the flexible housing are equivalent to that of the encapsulation of the non-disposable dry electrode mentioned above, and it is an integral-forming structure. Since the circuit module is packaged in the housing, it is prominently necessary for the physiological multi-parameter monitoring equipment to achieve a higher waterproof grade.

The specific working principle of the monitoring equipment is that the contact surface layers 1 on the first electrode 51 and the second electrode 52 are adhered to the skin, and connected to the external signal monitoring equipment through the extraction electrode 3, then a physiological signal acquired from the surface of human body can be received by the external signal monitoring equipment. Since the encapsulation is provided with the flexible silica gel 23, the whole dry electrode is flexible and can be closely fitted with the skin of the tested person, thereby increasing the contact area between the electrode and the skin, reducing the contact impedance and noise, and improving the acquisition quality of the physiological electrical signals.

The rear surface of the housing 5 is further provided with an upper cover detachably and sealably mounted; the upper cover is mounted in a circular groove 105 disposed on the rear surface of the housing 5 by being embedded into a waterproof ring by means of thread matching, and the fastened upper cover 101 is tightly pressed on the flexible material of the housing 5 to form a waterproof seal. The upper cover is internally provided with a battery which is electrically connected with the circuit module in the housing 5 through a gold-plated or gold-immersed metal sheet embedded into the upper cover and metal contacts correspondingly disposed on the housing 5; the battery is a rechargeable battery or can be taken out from the housing for charging. A surface of the housing 5 covered by the upper cover is provided with an internal storage card slot for inserting an internal storage card, and the internal storage card slot is connected with the circuit module for storing the acquired and processed physiological parameter data into the internal storage card.

The upper cover is designed to be detachable, and the internal storage card for storing data can be seen after the upper cover is detached. The internal storage card can be taken out and connected with a computer to conveniently export data. The wireless communication interfaces such as a 4G/5G wireless communication module, a Bluetooth module, a WIFI module, etc. are embedded into a circuit in the housing to carry out data transmission with a computer or terminal equipment. The battery is placed in the upper cover. After being aligned with the opening of the housing, the upper cover can be screwed into the housing.

If the battery is exhausted while in use, the user may choose to remove the upper cover and replace the battery or directly replace the upper cover with a standby upper cover having a battery of enough power, without removing the main body of the patch-type physiological multi-parameter monitoring equipment, so that the interruption time is short, and the continuity of signal acquisition is relatively ensured. The battery is placed in the upper cover, so that the battery can be conveniently replaced when it is damaged; meanwhile, when the battery is to be charged, a special charging device can be employed for charging through the contacts reserved in the upper cover after the upper cover is removed, without needing to additionally provide a charging port outside the main body of the patch-type physiological multi-parameter monitoring equipment, thus further improving the sealing and waterproof performance.

The upper cover is mounted in a groove disposed on the rear surface of the housing, and the fastened upper cover is tightly pressed on the flexible material of the housing to achieve waterproofness; preferably, the upper cover is screwed in the circular groove disposed on the rear surface of the housing by means of thread matching.

In this embodiment, the physiological multi-parameter monitoring equipment and the non-disposable dry electrode further comprise a double-sided glue layer, also known as a self-adhesive patch, which is adhered to the front surface of the housing, for the purpose of being firmly adhered to the human skin, especially when there is much sweat under the exercise conditions, thereby solving the problem of unreliable wearing in the prior art.

The following description is made in conjunction with the physiological multi-parameter monitoring equipment. The glue layer of the non-disposable dry electrode may be appropriately set with reference to the physiological multi-parameter monitoring equipment.

Figure 8:
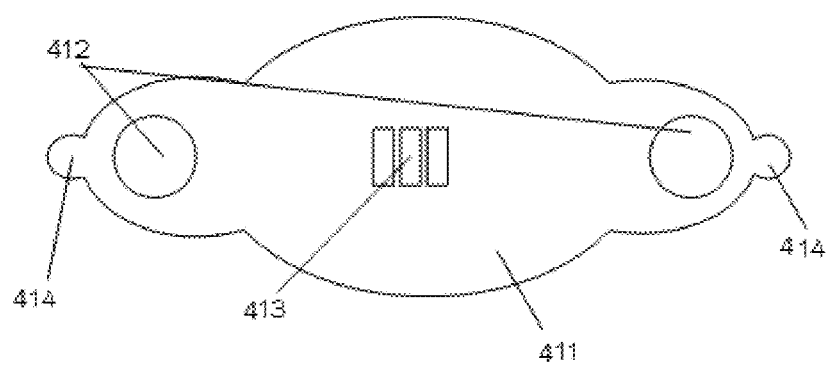
FIG. 8 is a bottom schematic diagram of a self-adhesive patch including the electrode through-hole and the sensor through-hole according to an embodiment of the present invention.

As illustrated in FIG. 8, the shape and size of the self-adhesive patch are consistent with those of the physiological multi-parameter monitoring equipment, comprising a non-woven double-sided adhesive tape 411, and two electrode through-holes 412 adhered to silica gel (not illustrated). The silica gel is matched with the through-hole in shape and size and it is aligned with the through-hole. The self-adhesive patch further comprises a sensor through-hole 413, which can be cooperated with a pulse wave sensor, a temperature sensor, etc. The two sides of the self-adhesive patch are respectively provided with gripping ears 414, which are non-adhesive and integrated with the non-woven double-sided adhesive tape 411, to facilitate the detachment of the non-adhesive film or release paper, or to tear off the self-adhesive patch from a signal acquisition target and/or signal acquisition equipment.

The shape and size of the self-adhesive patch is not limited to that illustrated in FIG. 8, and it may also be circular, square, rectangular, rhombus, etc. The self-adhesive patch may be matched with the signal acquisition equipment in shape and size, and its area may also be larger than that of the signal acquisition equipment.

In addition to the non-woven double-sided adhesive tape, a medical double-sided adhesive tape or nonpolar silica gel may also be used. The medical double-sided adhesive tape has a low production cost and a high safety, and it is advantageous for adhesion. When the nonpolar silica gel is removed from the skin, it will not cause damage to the fine hair and the skin and then reduce the pain.

The gripping ear may be disposed at any position around the self-adhesive patch, and is not limited to the two sides of the self-adhesive patch as illustrated in the drawings.

In the physiological multi-parameter monitoring equipment provided by this embodiment, a housing made of a flat flexible material and integrated with a pulse wave sensor is formed through a liquid silica gel injection molding or a solid silica gel compression molding, and a circuit module for processing the acquired physiological parameter data is sealed in the housing. According to the integrated design, the housing can be conveniently adhered to the human body through the medical double-sided adhesive tape, so that the wearing comfort and simplicity for the human body are improved, and the patch-type physiological multi-parameter monitoring equipment is also convenient to be worn and used.

Embodiment 2

Figure 1:
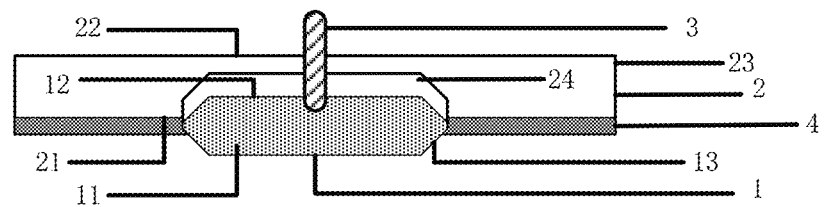
FIG. 1 is a full profile diagram of a waterproof dry electrode according to an embodiment of the present invention.
Figure 2:
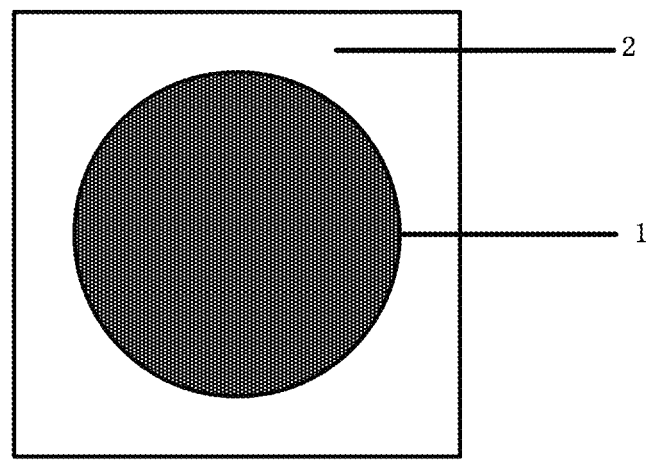
FIG. 2 is a bottom view I of a non-disposable dry electrode or a waterproof dry electrode according to an embodiment of the present invention.
Figure 3:
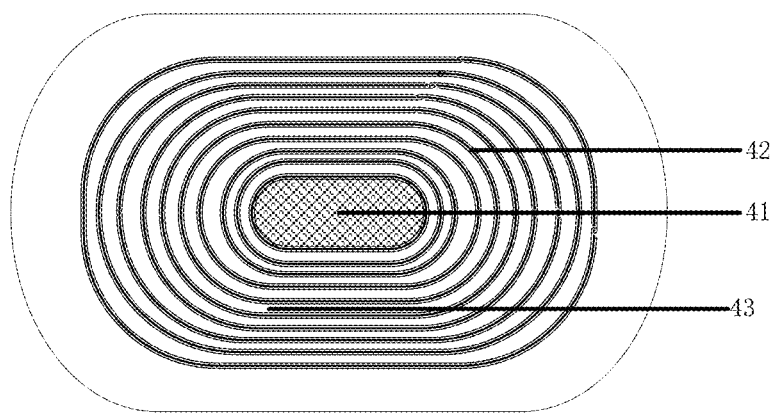
FIG. 3 is a bottom view II of a non-disposable dry electrode or a waterproof dry electrode according to an embodiment of the present invention.

The non-disposable dry electrode provided in this embodiment is illustrated in FIG. 1 to and 3, and its basic structure, components and specific use principle are the same as those in Embodiment 1. The difference mainly lies in that the conductive material of the contact surface layer 1 is changed from metal to conductive silica gel.

In this embodiment, the encapsulation 2 is made of non-polar silica gel, which is a high-activity adsorption material. The contact surface layer in this embodiment is made of conductive silica gel, and the manufacturing method is that it is formed under a high temperature and a high pressure by directly mixing nickel-coated copper powder and conductive graphite into the encapsulation 2 made of non-polar silica gel, and seamlessly connected with the encapsulation 2 with good water vapor tightness, thereby can be used in water.

The conductive silica gel is strongly self-adhesive, and highly stable when being adhered to the skin rather than easy to fall off. It has no toxicity, no sensitization or no irritation and is safe for use.

The conductive silica gel, which employs nickel-coated copper powder and conductive graphite as conductive filling materials, has good electromagnetic shading effect and oxidation resistance, and strong corrosion resistance under acid and alkali environments, thus increasing the service life of electrode. Of course, other materials may also be selected as conductive filling materials according to the actual situation, such as silver powder, acetylene graphite, etc.

The exposed part 11 of the contact surface layer 1 is provided with protruded textures 42, and a groove 43 is formed between the adjacent textures 42. In this embodiment, the textures are annularly disposed by taking the contact surface layer as a center. The textures 42 are made of the same conductive silica gel material as 41, and the protrusions increase the friction between the first surface 21 of the dry electrode and the skin, and also play an advantageous role for perspiration. When the human body takes exercises, the grooves 43 between the protruded textures 42 will be full of sweat, which makes the adhesion between the electrode and the skin be tighter and firmer, and the sweat also acts as a dielectric to improve the electrical conductivity.

Most of the area of the exposed part 11 of the contact surface layer 1 at the center of the first surface 21 of the dry electrode is adhered to the skin by the flexibility of the conductive silica gel, and only a small area of the first surface 21 on a periphery of the contact surface layer 1 is adhered to the skin by the double-sided adhesive tape. Thus, the dry electrode using conductive silica gel can be repeatedly adhered to the skin for many times, and no damage will be caused to the patient's fine hair and skin when the electrode is removed, thereby reducing the pain.

A portion of the extraction electrode 3 located in the encapsulation 2 and connected to the embedded part 12 of the contact surface layer 1 is made of conductive silica gel. The extraction electrode at the center of the second surface 22 of the encapsulation 2 is provided with a reinforcing tendon for reinforcing a connection between the RF shading wire and the extraction electrode 3, thereby improving a connection toughness of the extraction electrode 3 at the center of the second surface 22 and preventing the wire from being bent. The reinforcing tendon is made of the same silica gel material as that of the encapsulation 2 and is integrally connected with the second surface 22 of the encapsulation to surround the extraction electrode 3.

The electrical properties of the wet electrode and the conductive silica gel are tested and compared according to a Chinese medicine industry standard YY/T 0196-2005 Disposable ECG Electrodes, wherein a glue-to-glue impedance of the wet electrode is usually several thousand ohms, while that of the conductive silica gel is only a few hundred ohms; the DC offset voltage of the conductive silica gel is only 0.1 mV, which is far less than 94.8 mV; after a stable period of one minute of the glue-to-glue electrode, the composite offset unstable noise of the conductive silica gel is 0.9 to 1.1 mV, which is slightly smaller than that (1.5 to 1.7 mV) of the wet electrode; during a bias current tolerance test for the direct current, a voltage of the conductive silica gel always remains unchanged at about 0 mV, while a voltage of the wet electrode is alternately positive and negative from 49.8 mV.

Embodiment 3

Figure 9:
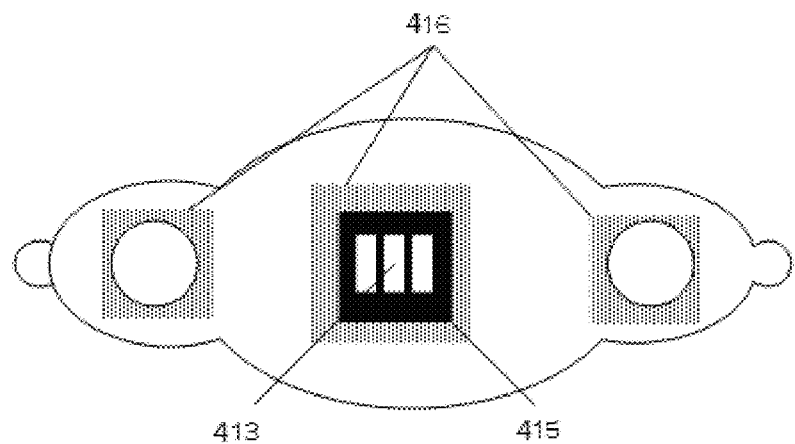
FIG. 9 is a bottom schematic diagram of a self-adhesive patch including black UV glue and a miniature sucker array according to an embodiment of the present invention.

FIG. 9 illustrates another embodiment of a bottom surface of a self-adhesive patch. In addition to all the components in Embodiment 1, a black UV glue 415 and a miniature sucker array 416 are disposed around a sensor through-hole 413; through the black UV glue, the light around an LED of the sensor can be shielded, thereby effectively avoiding the optical crosstalk between different LEDs, and improving the acquisition quality of signals such as pulse waves. The black UV glue has the advantages of high shading rate, strong adhesive force, quick UV curing speed and being suitable for the assembly line production. The miniature sucker array 416 can enhance the adhesion between the periphery of the through-hole and the skin; especially for a thin body user, due to the influence of protruding ribs and sunken skin, ordinary suckers cannot be adsorbed on the skin surface; while the miniature sucker array can effectively overcome this problem due to the small sucker area and the large sucker number.

The sensor through-hole 413 may be used for not only acquisition of pulse waves, but also a skin characteristic sensor. The light emitting device of the skin characteristic sensor consists of three independent and non-interfering light sources, namely RGB white light, polarized light and ultraviolet light. The black UV glue functions to isolate the three light sources.

In addition to the black UV glue, any other glue or device capable of blocking light may also be disposed around the sensor through-hole.

Embodiment 4

Figure 10:
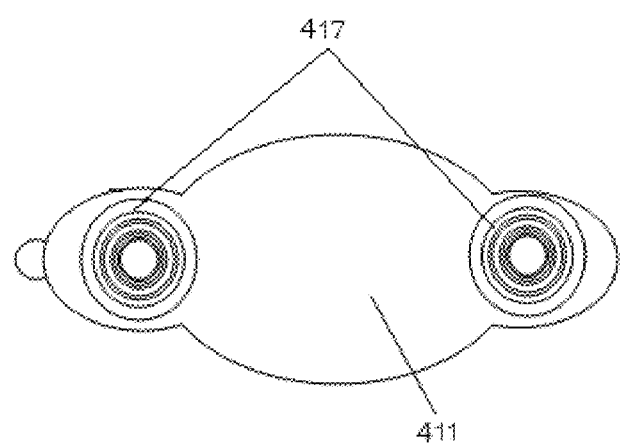
FIG. 10 is a bottom schematic diagram of a self-adhesive patch including silica gel provided with protruded textures according to an embodiment of the present invention.

FIG. 10 illustrates another embodiment of the bottom surface of the self-adhesive patch. The self-adhesive patch comprises a non-woven double-sided adhesive tape 411, and two electrode through-holes (shielded by the silica gel). The silica gel is adhered to the electrode through-holes, protruded textures 417 are disposed on a surface of the silica gel, and a groove is formed between the adjacent textures.

The protruded textures increase the friction between the solid gel or the conductive silica gel and the skin, and also play an advantageous role for perspiration. Especially when the human body takes exercises, the grooves between the protruded textures will be full of sweat, which makes the adhesion between the solid gel or the conductive silica gel and the skin to be tighter and firmer, and the sweat acts as a dielectric to improve the electrical conductivity. The conductivity rises as the sweat increases, and it is more suitable for use in exercises.

As the sweat will accumulate in the grooves between the textures 417, a large number of micropores can be disposed in the grooves and filled with hydrophilic porous media. When a sweat acquisition sensor is contacted with the textures 417, the sweat will be acquired by the sensor through the porous media with good water absorption.

Embodiment 5

Figure 11:
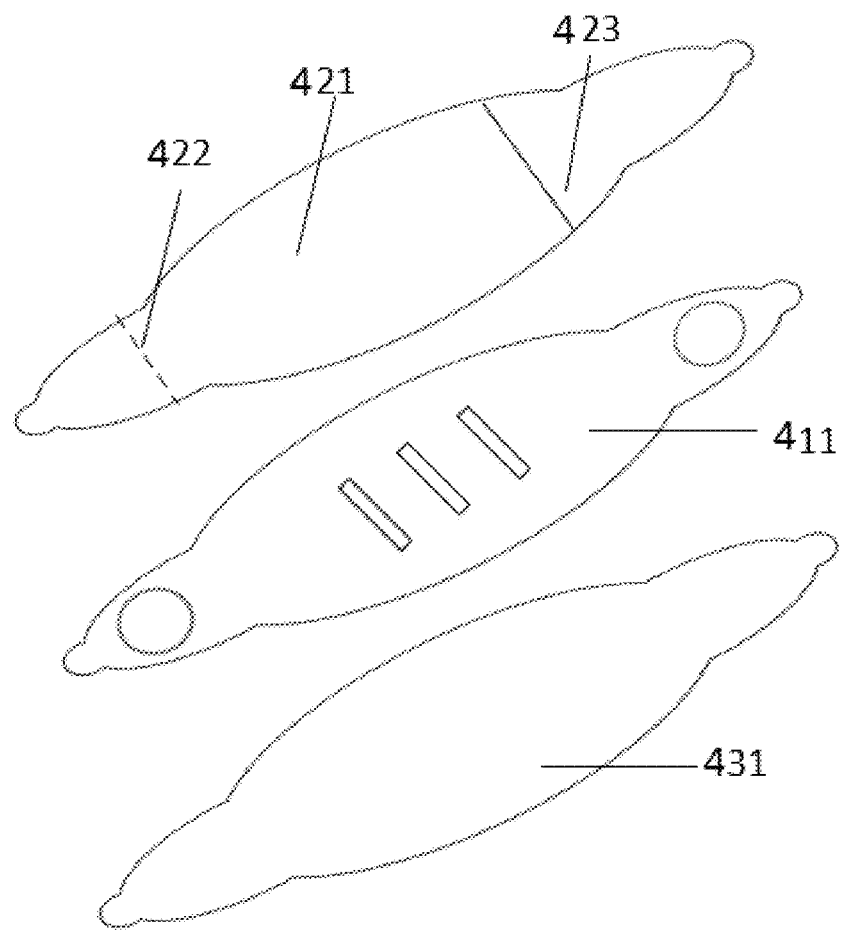
FIG. 11 is an exploded diagram of a self-adhesive patch according to an embodiment of the present invention.

FIG. 11 illustrates an exploded diagram of a self-adhesive patch, comprising a first-type release layer 421, a non-woven double-sided adhesive tape 411 including through-holes, and a second-type release layer 431 from top to bottom in sequence. The first-type release layer 421 is attached to a rear surface of the self-adhesive patch, i.e., the self-adhesive patch needs one side to be adhered to the acquisition equipment; the second-type release layer 431 is adhered to a bottom surface of the self-adhesive patch, i.e., the self-adhesive patch needs one side to be adhered to the human skin. The first-type release layer 421 is a segmented structure, and the segmentation is made between the through-holes of the self-adhesive patch, wherein 422 denotes an easily-torn line, and 423 denotes a gap line. When the patch is to be used, the left electrode through-hole is aligned with the electrode of the physiological multi-parameter acquisition equipment firstly, and after an accurate alignment, the segmented release layer on the left side of the easily-torn line is detached; next, the middle sensor through-hole is aligned with the sensor of the physiological multi-parameter acquisition equipment, and after an accurate alignment, the middle segmented release layer is detached; next, the right electrode through-hole is aligned with the electrode of the physiological multi-parameter acquisition equipment, and after an accurate alignment, the segmented release layer on the right side of the gap line is detached. The self-adhesive patch can be adhered to the acquisition equipment at one time by means of sequential alignments, and the through-holes are matched with the electrodes or the sensor, thereby avoiding the problem of repeated alignment. Finally, the second-type release layer 431 is detached and adhered to the human skin.

One or more easily-torn lines or gap lines may be disposed on the segmented release layer, and between corresponding through-holes. The easily-torn line or the gap line may be disposed in segments between all of the through-holes so that each through-hole can be accurately aligned, or between some of the through-holes.

Embodiment 6

Figure 12:
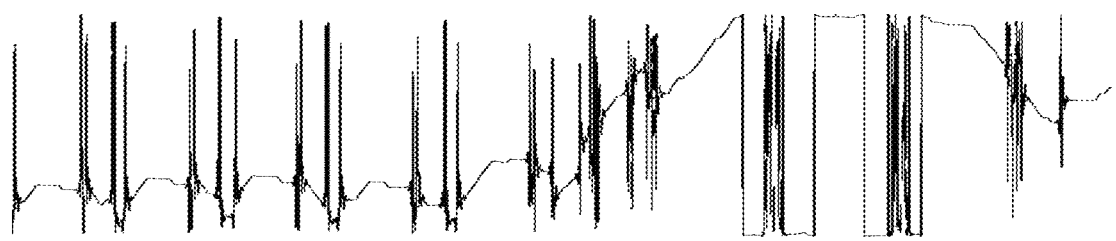
FIG. 12 is an electrocardiogram using a metal electrode according to an embodiment of the present invention.

Similarly, the human body is under the condition of mild exercise (non-strenuous exercise), the ECG acquisition equipment is adhered to the chest of the human body for ECG acquisition, and the comparative test results are as follows:

FIG. 12 illustrates ECG signals acquired by an ECG acquisition from a human body using an ECG acquisition equipment with a metal electrode, wherein the disposable self-adhesive patch as described above is not adhered to the metal electrode.

Due to the slight movement of the human body, the skin can be stretched or contracted, while the metal has poor flexibility and self-adhesion, and the stretching performance is limited. Thus, the electrode is moved relative to the skin, rather than being tightly fitted with the skin, which will produce severely distorted ECG signals.

Figure 13:
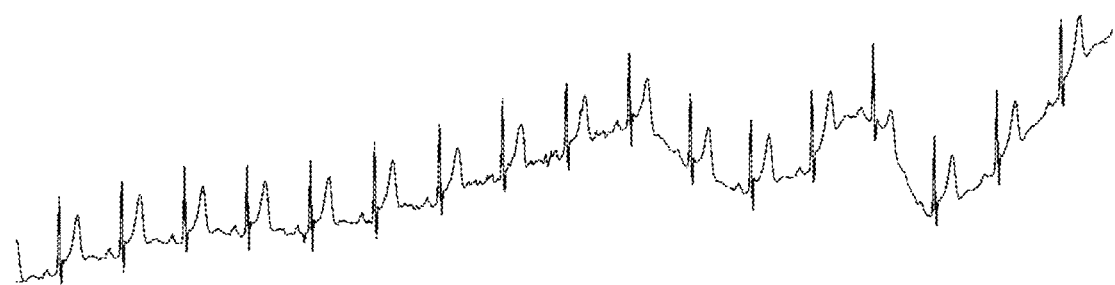
FIG. 13 is an electrocardiogram using a metal electrode and a self-adhesive patch according to an embodiment of the present invention.

FIG. 13 illustrates ECG signals acquired by an ECG acquisition from a human body using an ECG acquisition equipment with a metal electrode, wherein a disposable self-adhesive patch is adhered to the metal electrode, the bottom of the electrode hole is hollowed out and the conduction medium is not pasted.

As can be seen from the FIG. 13, the electrode is tightly fitted with the skin by the adhesion of the self-adhesive patch, and the quality of signal acquisition is improved. Except baseline drift and slight EMG noise, the signal waveform will not be distorted.

Figure 14:
FIG. 14 is an electrocardiogram using an ordinary wet electrode according to an embodiment of the present invention.

FIG. 14 illustrates ECG signals acquired by an ECG acquisition from a human body using an ECG acquisition equipment with an ordinary wet electrode, wherein the disposable self-adhesive patch as described above is not adhered to the ordinary wet electrode, and the ECG signal contains obvious EMG noise (burr).

Since the ordinary wet electrodes are two electrodes additionally led out from the ECG acquisition equipment and directly adhered to the human skin, they cannot be adhered to the patch, and there is no comparative test.

Figure 15:
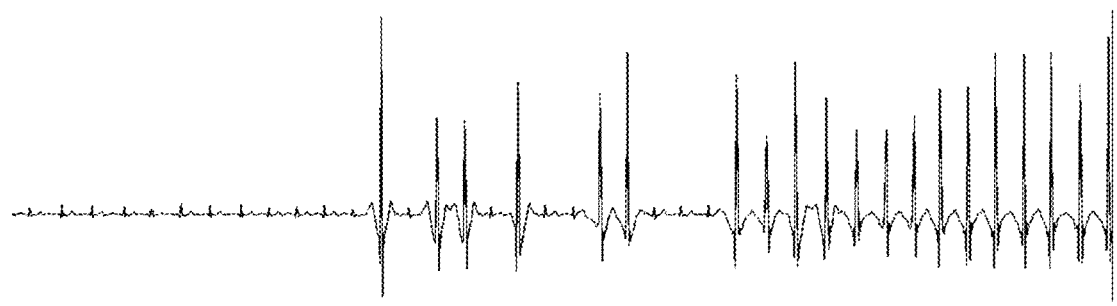
FIG. 15 is an electrocardiogram using a conductive silica gel electrode according to Embodiment 5 of the present invention.

FIG. 15 illustrates ECG signals acquired by an ECG acquisition from a human body using an ECG acquisition equipment with a conductive silica gel electrode, wherein the disposable self-adhesive patch as described above is not adhered to the conductive silica gel electrode.

The waveforms with smaller amplitudes in the figure are the signals that should be acquired under normal conditions, while those with larger amplitudes are abnormal. There is almost no EMG noise in the signal, but the amplitude of the signal will change abruptly. This is because the conductive silica gel does not fit tightly with the skin when there is no other self-adhesive conductive medium.

Figure 16:
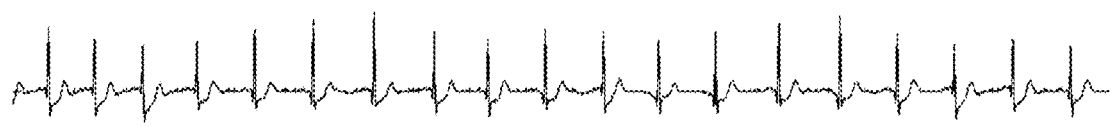
FIG. 16 is an electrocardiogram using a conductive silica gel electrode and a self-adhesive patch according to an embodiment of the present invention.

FIG. 16 illustrates ECG signals acquired by an ECG acquisition from a human body using an ECG acquisition equipment with a conductive silica gel electrode, wherein a disposable self-adhesive patch is adhered to the conductive silica gel electrode, a conductive medium is adhered to the bottom surface of the electrode through-hole of the self-adhesive patch, and the conductive medium is solid gel or conductive silica gel. As compared with FIG. 15, the signals almost have no EMG noise or abnormal waveform, and the signal quality is significantly improved.

In a preferred embodiment, a self-adhesive patch as illustrated in FIG. 10 is adhered to the ECG acquisition equipment, and silica gel with textures is adhered to the electrode through-hole of the patch, and the ECG acquisition effect at this time is similar to that of FIG. 16.

In another preferred embodiment, a self-adhesive patch is adhered to the ECG acquisition equipment, and conductive silica gel with textures is adhered to the electrode through-hole of the patch; a liquid conductive medium is filled in the textures before the ECG signal acquisition, for example, mineral water is used to coat the conductive silica gel, and the ECG acquisition effect at this time is similar to that of FIG. 16.

In another preferred embodiment, a self-adhesive patch is adhered to the ECG acquisition equipment, and two layers of conductive media are adhered to the electrode through-hole of the patch, wherein one layer is conductive silica gel which is adhered to a double-sided adhesive tape; the other layer is silica gel, with one side adhered to the conductive silicon glue layer, and the other side in contact with human skin. The ECG acquisition effect at this time is similar to FIG. 16.

Through the comparisons between FIG. 12 and FIGS. 13, 15 and 16, it can be seen that the signal acquired after adding the self-adhesive patch is obviously better than the previous signal.

The electrical properties of the wet electrode and the conductive silica gel are tested and compared according to a Chinese medicine industry standard YY/T 0196-2005 Disposable ECG Electrodes. The experimental results are listed below. It can be seen that the electrical properties of conductive silica gel are significantly better than those of the ordinary wet electrode, thus explaining to some extent that the signal acquisition effect of the self-adhesive patch using solid gel and conductive silica gel is significantly better than that of the ordinary wet electrode. From the above comparison, it can be seen that the EMG noise in the signal of FIG. 16 is basically eliminated.

| Test item | Category | | | Result comparison |
| --- | --- | --- | --- | --- |
| | Wet electrode | Conductive silica gel | Criterion | |
| AC impedance | The resistance value changes rapidly. In about 4 minutes, the resistance value decreases from 403.2 ohms to 359 ohms, and then increases rapidly to 404.2 ohms | The resistance value changes slowly, decreasing from 63.4 ohms to 56.9 ohms within the observation time (1 hour) | The average impedance does not exceed 2 KΩ, and the impedance of individual glue-to-glue electrode does not exceed 3 KΩ | The AC impedance of the conductive silica gel glue-to-glue electrode is smaller than that of the wet electrode |
| DC offset voltage | 94.8 mV | 0.1 mV | After a one-minute stable period, the offset voltage is not more than 100 mV | The DC offset voltage of the conductive silica gel is significantly lower than that of the wet electrode |
| Bias current tolerance | From −49.8 mV, the negative voltage decreases to 0 at a change rate of | The voltage is always kept at 0 mV without any change. | 200 nA direct current is applied, the observed voltage | The bias current tolerance of the conductive silica gel is |

| Test item | Wet electrode | Conductive silica gel | Criterion | Result comparison |
|---|---|---|---|---|
| | about 0.1 mV/s, and then the positive voltage increases at a rate of 0.005 mV/s; after increasing to 11.2 mV, the voltage changes again to be negative and the change rate gradually decreases. | | variation across the electrode pair over the entire duration is not more than 100 mV. | better than that of the wet electrode |

Embodiment 7

As compared with any of the above embodiments, the waterproof structure added in this embodiment is a waterproof dry electrode, and the difference lies in that the encapsulation 2 comprises flexible silica gel 23 and hard plastic portion 24, the embedded part 12 is embedded into the hard plastic portion 24, and the hard plastic portion 24 is packed in the flexible silica gel 23.

Figure 6:
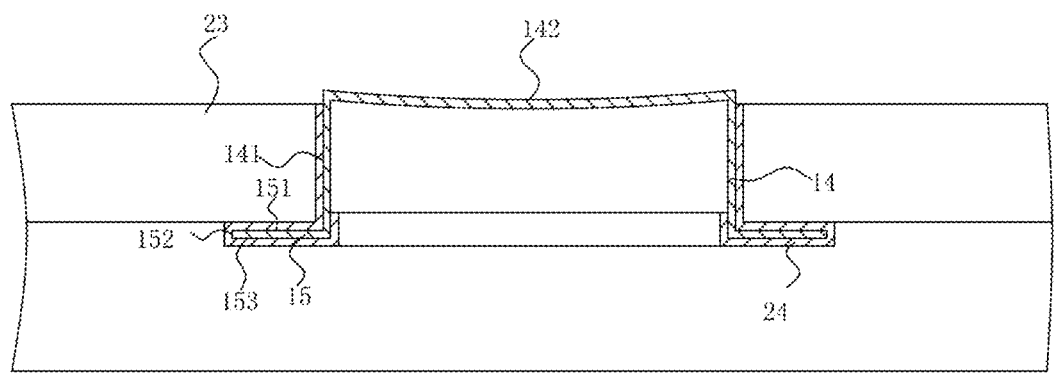
FIG. 6 is a schematic diagram I of the encapsulation structure for the contact surface layer according to an embodiment of the present invention.

In order to facilitate the mounting of the contact surface layer, the contact surface layer 1 in FIG. 6 comprises a contact surface body 14 and a limiting flange 15 which are integrally formed, wherein the limiting flange 15 protrudes from the outer side wall of the contact surface body 14, and at the same time, the waterproof effect will be better by combining the contact surface body 14 and the limiting flange 15 with the hard plastic portion 24.

Generally speaking, as illustrated in FIG. 6, only the front surface 142 of the contact surface body 14 is exposed after the encapsulation is completed, so the front surface 142 of the contact surface body 14 is an exposed part. The rest of the structure will be embedded into the encapsulation, so the embedded part comprises the limiting flange 15 and portions of the contact surface body 14 except the front surface. The embedded part needs to be embedded with the hard plastic portion 24. At this time, the limiting flange 15 and the portions of the contact surface body 14 except the front surface 142 are embedded into the hard plastic portion 24, and a waterproof embedding surface is formed at a contact position with the hard plastic portion 24, because the limiting embedding surface is not one plane, but is formed by combining a plurality of planes or curved surfaces, i.e., the outer side wall surface 141 of the contact surface body 14, the front surface 151 of the limiting flange 15, the outer side wall surface 152 of the limiting flange 15 and the rear surface 153 of the limiting flange 15. Therefore, the formed boundary is tortuous, and it is more difficult for the liquid to enter the tortuous boundary. By utilizing the material characteristics of the hard plastic portion 24, the first electrode or the second electrode can have a good bonding with the hard plastic portion, thereby achieving a better waterproof effect with the aid of the tortuous boundary.

Figure 7:
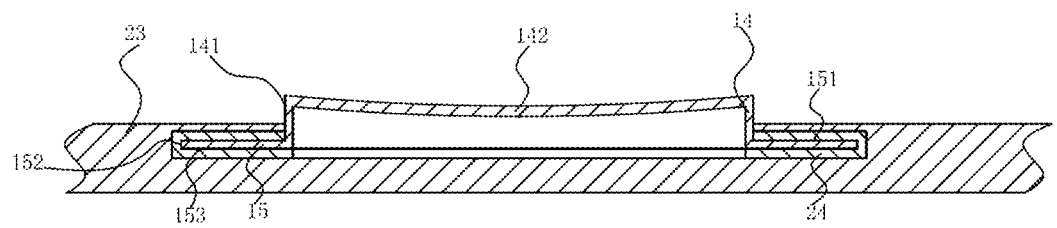
FIG. 7 is a schematic diagram II of the encapsulation structure for the contact surface layer according to an embodiment of the present invention.

In some alternative embodiments of this embodiment, as illustrated in FIG. 7, the entire contact surface body 14 is exposed after the encapsulation is completed, so the contact surface body 14 is the exposed part. Correspondingly, the limiting flange 15 will be embedded into the encapsulation, so the embedded part comprises the limiting flange 15. The limiting flange 15 is embedded into the hard plastic portion 24 to form a waterproof embedding surface at the contact position with the hard plastic portion 24. The waterproof embedding surface is also not one plane, but is formed by combining a plurality of planes or curved surfaces, i.e., the front surface 151 of the limiting flange 15, the outer side wall surface 152 of the limiting flange 15 and the rear surface 153 of the limiting flange 15, so the boundary is also tortuous, and a better waterproof effect can be achieved.

Since the bonding surface of the hard plastic portion 24 and the embedded part is tortuous, the overall appearance of the hard plastic portion 24 is matched with the overall appearance of the embedded part correspondingly, so that the contact surface of the flexible silica gel 23 and the hard plastic portion 24 can also be tortuous, thereby increasing the contact area between the flexible silica gel and the hard plastic portion 24 and improving the waterproof effect.

The contact surface layer is embedded into the hard plastic portion, and then the contact surface layer provided with the hard plastic portion is packaged, so that as compared with the existing contact surface layer, the connection between the encapsulation and the contact surface layer is tighter, the bonding is stronger, and the waterproofness is improved for the reason that the direct connection between the contact surface layer and the flexible silica gel often cannot ensure a tight connection or bonding between the flexible silica gel and the contact surface layer due to the difference in the respective characteristics of the materials; through the arrangement of the hard plastic portion, a connection bridge can be established between the flexible silica gel and the contact surface layer, because both the contact surface layer and the flexible silica gel can have a strong bonding with the hard plastic portion, thereby solving the problem that the liquid can easily leak from the bonding surface due to the poor waterproof performance between the contact surface layer and the encapsulation. Through the above arrangement, the dry electrode can reach a waterproof grade of IPX7, which is higher than living waterproof grade of an ordinary dry electrode.

In addition, as illustrated in FIGS. 4-5, the physiological multi-parameter monitoring equipment of this embodiment differs in that the first electrode 51 and the second electrode 52 are any waterproof dry electrodes described above. In this embodiment, the characteristics of the flexible housing are equivalent to that of the encapsulation of the waterproof dry electrode, and the housing is an integral-forming structure.

The demand for the physiological multi-parameter monitoring equipment to achieve a higher waterproof grade is even more prominent because the circuit module is packaged in the housing. As compared with the traditional electrocardiograph, electromyogram, electroencephalograph, etc., the physiological multi-parameter monitoring equipment has the following innovation points:

1. The equipment is integrated into a patch, is ultra-small, ultra-thin and ultra-light, can be directly adhered to a surface of a human body, can perform dynamic real-time acquisition of physiological parameter signals, is comfortable to paste for a long time, and can be used in exercises, shower, swimming and various life scenes;

2. The dry electrode is adopted and can be reused for many times. Through the above arrangement, the dry electrode can reach a waterproof grade of IPX7, which is higher than living waterproof grade of an ordinary dry electrode.

3. The reusable dry electrode is combined with the self-adhesive patch of the medical double-sided adhesive tape; one side is adhered to the soft silica gel of the main machine of the equipment, and the other side is adhered to the skin surface of the chest of the human body, so as to ensure the close fit between the equipment and the skin. Even if the human body moves frequently in an exercise state, the human engineering design can ensure the comfort and long-term for pasting. The self-adhesive patch of the special medical double-sided adhesive tape ensures that the waterproof wearing will not fall off when the user is showering. The flexible silica gel and the self-adhesive patch of the double-sided adhesive tape adopted with the dry electrode, pass through strict biological compatibility tests, are made of medical-grade material, thus are safer to be worn. At the same time, the ECG paster adopt the dry electrode and the self-adhesive patch of the medical double-sided adhesive tape to replace the traditional disposable button type wet electrode sheet, thus reducing the use cost for the users, realizing the goal of the long-term comfortable wearing and dynamic real-time monitoring of the ECG by the users, with a very important clinical application value.

From the traditional monitoring equipment to the personal or family monitoring equipment, the biggest change is not only to monitor in a static environment, but also to perform the parameter monitoring in an exercising state, in which the human body sweats a lot during wearing; on one hand, the equipment cannot be worn for a long time and is easy to fall off; on the other hand, the acquisition electrodes need to be reused for many times to meet the needs of personal long-term parameter monitoring. Finally, due to the need of repeated use for many times, the exposed dry electrode becomes the first choice, and the waterproof is a subsequent problem caused by the large amount of sweat and the exposed dry electrode.

As stated above, the hard plastic portion is used to solve this problem. Accordingly, on this integrated parameter monitoring equipment, the waterproof dry electrode will greatly improve the waterproof performance. Therefore, during the personal monitoring, the dynamically monitored environment will be further extended, for example including swimming, etc., which will greatly facilitate the use of users and monitor the health of individuals at all times.

The rear surface of the housing 5 may be further provided with an upper cover detachably and sealably mounted; the upper cover is mounted in a circular groove 105 disposed on the rear surface of the housing 5 by being embedded into a waterproof ring by means of thread matching, and the fastened upper cover is tightly pressed on the flexible material of the housing 5 to form a waterproof seal. The upper cover is internally provided with a battery which is electrically connected with the circuit module in the housing 5 through a gold-plated or gold-immersed metal sheet embedded into the upper cover and metal contacts correspondingly disposed on the housing 5; the battery is a rechargeable battery or can be taken out from the housing for charging. A surface of the housing 5 covered by the upper cover is provided with an internal storage card slot for inserting an internal storage card, and the internal storage card slot is connected with the circuit module for storing the acquired and processed physiological parameter data into the internal storage card.

If the battery is exhausted while in use, the user may choose to remove the upper cover and replace the battery or directly replace the upper cover with a standby upper cover having a battery of enough power, without removing the main body of the patch-type physiological multi-parameter monitoring equipment, so that the interruption time is short, and the continuity of signal acquisition is relatively ensured. The battery is placed in the upper cover, so that the battery can be conveniently replaced when it is damaged; meanwhile, when the battery is to be charged, a special charging device can be employed for charging through the contacts reserved in the upper cover after the upper cover is removed, without needing to additionally provide a charging port outside the main body of the patch-type physiological multi-parameter monitoring equipment, thus further improving the sealing and waterproof performance.

The upper cover is mounted in a groove disposed on the rear surface of the housing, and the fastened upper cover is tightly pressed on the flexible material of the housing to achieve waterproofness; preferably, the upper cover is screwed in the circular groove disposed on the rear surface of the housing by means of thread matching.

This physiological multi-parameter monitoring equipment greatly improves the waterproof and sealing performance, and thoroughly solves the problem that the existing physiological multi-parameter monitoring equipment cannot be used during showering.

Embodiment 8

Referring to FIGS. 5 to 23, in one embodiment, a patch-type ECG acquisition equipment comprises a housing 5 made of a flat flexible material suitable for being adhered to a human skin, and a front surface of the housing 5 is provided with a first electrode 51 and a second electrode 52 for acquiring ECG signals by being adhered to the human skin; the housing 5 is integrally formed with the first electrode 51 and the second electrode 52 through a liquid silica gel injection molding or a solid silica gel compression molding; the circuit module for processing acquired ECG data is sealed in the housing 5, and is connected with the first electrode 51 and the second electrode 52.

The electrode may be a sheet-like metal dry electrode, and further, a material thereof may be medical-grade stainless steel, a copper sheet, a nickel strip, iron or manganese steel.

The electrode may also be a conductive silica gel electrode, i.e., conductive particles such as nickel-coated copper powder and silver powder are uniformly mixed into the silica gel, and conductive graphite and acetylene carbon black can also be added.

The electrode may also be a wet electrode sheet. The wet electrode sheet is mounted to the housing 5 in a replaceable manner by a wet electrode mounting structure (such as a fastener) provided on the housing 5. The wet electrode mounting structure can be integrally formed with the housing 5 by liquid silica gel injection molding or solid silica gel compression molding.

In a preferred embodiment, the patch-type ECG acquisition equipment further comprises an upper cover 101 detachably and sealably mounted on a rear surface of the housing 5, wherein a battery is disposed in the upper cover 101, and electrically connected with the circuit module in the housing 5 through the upper cover 101 and correspondingly disposed metal contacts 401 on the housing 5; and the battery is a rechargeable battery or a disposable battery that can be taken out from the upper cover 101 for replacement.

In a preferred embodiment, the upper cover 101 is mounted into a circular groove 105 disposed on the rear surface of the housing 5 by means of thread matching, and the fastened upper cover is tightly pressed on a flexible material of the housing 5 to achieve waterproofness.

In a preferred embodiment, a surface of the housing 5 covered by the upper cover 101 is provided with an external storage card slot 6 for inserting an external storage card, and the external storage card slot 6 is connected with the circuit module to store ECG data acquired and processed by the circuit module into the external storage card.

In a preferred embodiment, the housing 5 has a circular arc-shape, which is wide at the middle portion, and gradually narrowed towards two sides; the upper cover 101 is located at a middle portion of the housing 5, the first electrode 51 and the second electrode 52 are located at two sides of the upper cover 101, respectively.

In a preferred embodiment, the patch-type ECG acquisition equipment further comprises a temperature sensor 7 disposed on the front surface of the housing 5, wherein the housing 5 is integrally formed with the temperature sensor 7 through a liquid silica gel injection molding or a solid silica gel compression molding, and the temperature sensor 7 is configured to detect a body temperature and transmit acquired body temperature information to the circuit module.

In a preferred embodiment, the patch-type ECG acquisition equipment further comprises an attitude sensor disposed in the housing 5 and configured to acquire motion and direction data to judge a motion state of a user; the attitude sensor may be a three-axis sensor (e.g., a three-axis accelerometer or a gyroscope), a six-axis sensor (e.g., a three-axis accelerometer and a three-axis gyroscope) or a nine-axis sensor (e.g., a three-axis accelerometer, a three-axis gyroscope and a three-axis magnetic induction sensor).

In a preferred embodiment, the patch-type ECG acquisition equipment further comprises a wireless communication module disposed in the housing 5, such as a Bluetooth module, wherein the wireless communication module is configured to wirelessly transmit the ECG data processed by the circuit module to a terminal.

In a preferred embodiment, the patch-type ECG acquisition equipment further comprises an alarm device, such as a vibration motor which is preferably disposed in the housing 5 or a position on a wall of the housing 5 corresponding to the first electrode and/or the second electrode; the vibration motor is connected with the circuit module, and configured to generate a vibration alarm under set conditions, wherein the set conditions include that the circuit module detects the battery low electric quantity or an abnormal heart rhythm.

In a preferred embodiment, the alarm device may also be a speaker which is connected with the circuit module, and configured to generate a sound alarm under set conditions, wherein the set conditions include that the circuit module detects the battery low electric quantity or an abnormal heart rhythm.

In a preferred embodiment, the patch-type ECG acquisition equipment further comprises other electrodes configured to acquire ECG signals, the other electrodes being led out from the upper cover or the housing through lead wires and electrically connected with the circuit module in the housing through the upper cover and correspondingly disposed metal contacts on the housing; and the other electrodes can form various ECG lead system together with the first electrode and the second electrode, including typical forms in the conventional 12-lead system, such as three-electrode one-lead, five-electrode seven-lead and complete ten-electrode twelve-lead, and a Frank lead system may also be formed. In some alternative embodiments of this embodiment, other electrodes may also be directly led out from the housing through lead wires.

In a specific embodiment, the patch-type ECG acquisition equipment comprises third to fifth electrodes 8 for acquiring ECG signals, wherein the third to fifth electrodes 8 are led out from the upper cover 101 through three lead wires, and are electrically connected with the circuit module in the housing 5 through the upper cover 101 and metal contacts 401 correspondingly disposed on the housing 5; and the third to fifth electrodes 8 form five-electrode seven-lead system together with the first electrode 51 and the second electrode 52.

In addition, the housing 5 is preferably provided with a power-on button 9.

The upper cover 101 is preferably provided with an emergency button 10, which can be pressed by a user in an emergency state to send an emergency alarm to the system backend.

The specific embodiments of the present invention and the advantages thereof will be further described below with reference to the drawings.

In a specific embodiment, a patch-type ECG acquisition equipment with a detachable self-adhesive tape on the dry electrodes is provided. The electrode is a metal dry electrode or a conductive silica gel electrode, and can be conveniently adhered to the human skin through a medical double-sided adhesive tape, so that it can be repeatedly used without causing irritation to the human skin. The patch ECG acquisition equipment can carry out long-term continuous ECG detection on the human body, and users can also choose a multi-lead mode as needed. At the same time, the equipment is also integrated with a temperature sensor and an attitude sensor to measure the user's body temperature and motion state.

As a part of the ECG monitoring system, the patch ECG acquisition equipment realizes the ECG data acquisition. The acquired ECG data can be wirelessly transmitted to the diagnosis terminal for arrhythmia analysis, or further transmitted to the cloud backend for arrhythmia analysis if necessary, and the analyses results will be returned.

Structurally speaking, the patch-type ECG acquisition equipment mainly comprises a flat flexible housing for being adhered to a human body, a circuit module is disposed in the housing, the front surface of the housing is provided with two sheet-like electrodes in contact with the human body and a temperature sensor for acquiring temperatures; the electrode sheets are located on both sides of the housing. The rest of the flexible housing is integrally sealed with an opening at the back surface, and an external storage card slot is disposed in the opening.

Additionally, there is a detachable upper cover in which a battery is sealed, and a front surface is provided with metal contacts connected with a circuit board in the housing. After being aligned with the opening of the housing, the upper cover may be screwed into the housing, and then a good sealing effect can be achieved due to the tight connection between the upper cover and the external flexible material. In an exemplary embodiment, in addition to the above parts, another three electrode lead wires may be integrated on the upper cover, thereby realizing a five-electrode seven-lead system.

The patch-type ECG acquisition equipment is provided with a temperature sensor and an attitude sensor, wherein the temperature sensor is configured to acquire a body temperature, and the attitude sensor for example is a three-axis acceleration sensor or a gyroscope for acquiring a motion state of a user. The circuit module acquires the ECG data of the user through the electrode sheets, processes the data through a data processing module therein and stores the processed data into the storage module, and finally transmits the processed data through a data transmission module. At the same time, due to the design of the detachable upper cover, the external storage card can be conveniently taken out to directly export the data to carry out a data analysis after the ECG data is acquired for one cycle.

A vibration motor is further disposed in the housing corresponding to the position of the electrode sheet, and the whole housing is formed using a liquid silica gel injection molding technology; and the housing fully packs the electrode sheets, the motor and the temperature sensor for sealing and waterproof.

Figure 20:
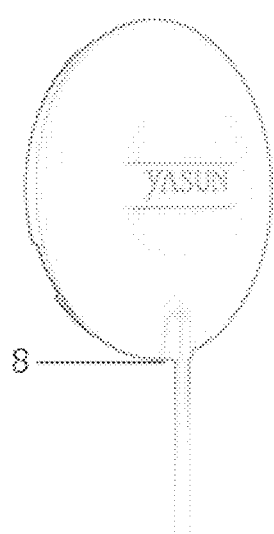
FIG. 20 is a schematic diagram of an upper cover (realizing multi-lead) with lead wires and an electrode according to Embodiment 8 of the present invention.

FIG. 4 illustrates that the whole ECG patch is just like one piece after the upper cover is buckled. The upper cover is designed as detachable, and an external storage card for storing data can be seen after the upper cover is removed; after the external storage card is taken out and connected with a computer, the data can be conveniently exported. The battery is placed in the upper cover. After being aligned with the opening of the housing, the upper cover may be screwed into the housing. At the same time, FIG. 20 illustrates an upper cover that realizing five-electrode and seven-lead, and additionally there are three lead wires outgoing from the upper cover.

The preferred embodiment adopts the design of a detachable upper cover, and the external storage card can be conveniently taken out for data copy after the upper cover is removed. If the battery is exhausted while in use, the user may choose to remove the upper cover and replace the battery or directly replace the upper cover with a standby upper cover having a battery of enough power, without removing the main body of the patch-type physiological multi-parameter monitoring equipment, so that the interruption time is short, and the continuity of signal acquisition is relatively ensured. The battery is placed in the upper cover, so that the battery can be conveniently replaced when it is damaged; meanwhile, when the battery is to be charged, a special charging device can be employed for charging through the contacts reserved in the upper cover after the upper cover is removed, without needing to additionally provide a charging port outside the main body of the patch-type physiological multi-parameter monitoring equipment, thus further improving the sealing and waterproof performance.

The preferred embodiment provides a multi-lead mode. Since many heart diseases represent the arrhythmia events only under certain leads, multi-lead ECG data can be provided to doctors for more comprehensive and accurate judgments. For the multiple leads, an upper cover design with additional lead wires is adopted, as illustrated in FIG. 20.

Specifically, the multiple leads can be in various typical forms according to a classic 12-lead system, such as ten-electrode twelve-lead, five-electrode seven-lead, three-electrode one-lead, etc.

Figure 21:
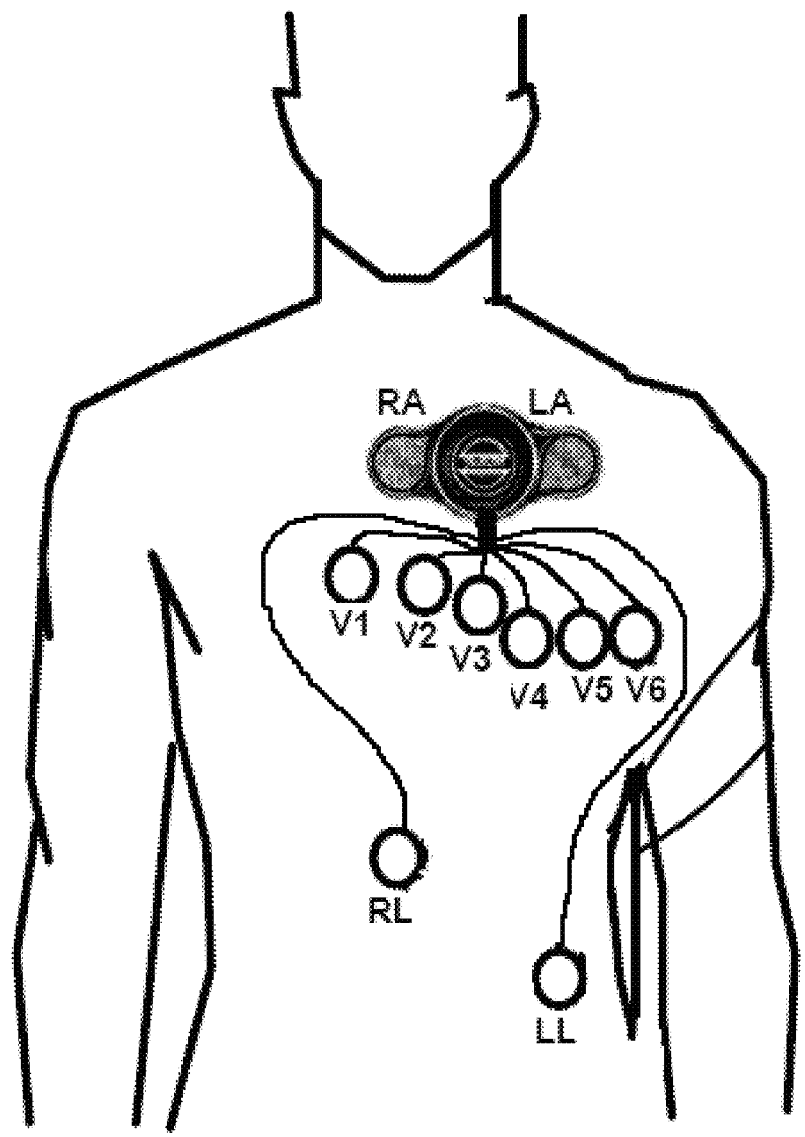
FIG. 21 is a diagram of connections using electrode leads according to Embodiment 8 of the present invention.

For the ten-electrode twelve-lead system (as illustrated in FIG. 21), when the user is in use, the first electrode on the front of the housing of the patch-type ECG acquisition device is RL, the second electrode is LL. In the other eight leads, two of the extraction electrodes are affixed to the first intercostal (RA) of the right sternal line of the right shoulder sternum and the first intercostal (LA) of the left sternal edge of the left shoulder sternum, respectively, and the remaining six leads are conventional 6 precordial leads. That is, affixed to the following six positions: V1, the fourth intercostal margin of the right margin of sternum; V2, the fourth intercostal of the left margin of sternum, V3, the midpoint of V4 line, V4, the fifth intercostal of left clavicle line, V5, the front line of left axil was the same level as V4, and the level of V6, left axillary midline and lead V4 are the same.

The standard twelve-lead ECG data thus measured are:

$$\text{Lead } II = LL - RA;$$

$$\text{Lead } III = \text{Lead } II - \text{Lead } I;$$

$$\text{Lead } V (V1 \text{ to } V6);$$

$$aVR = -(I+II)/2;$$

$$aVL = I - II/2;$$

$$aVF = II - I/2.$$

For the five-electrode seven-lead placement, RA, LA, LL and RL are all consistent with those of the above ten-electrode twelve-lead placement, except that the chest lead is selected from V1 to V6 as needed.

In addition, the multi-lead system can also be frank lead system, and its seven-electrode positions respectively are E at the anterior midline, M at the back midline, I at the right axillary midline, A at the left axillary midline, a midpoint C between E and A at the left chest, and the rest two electrodes are placed at the left lower limb as F and the neck as H.

Figure 22:
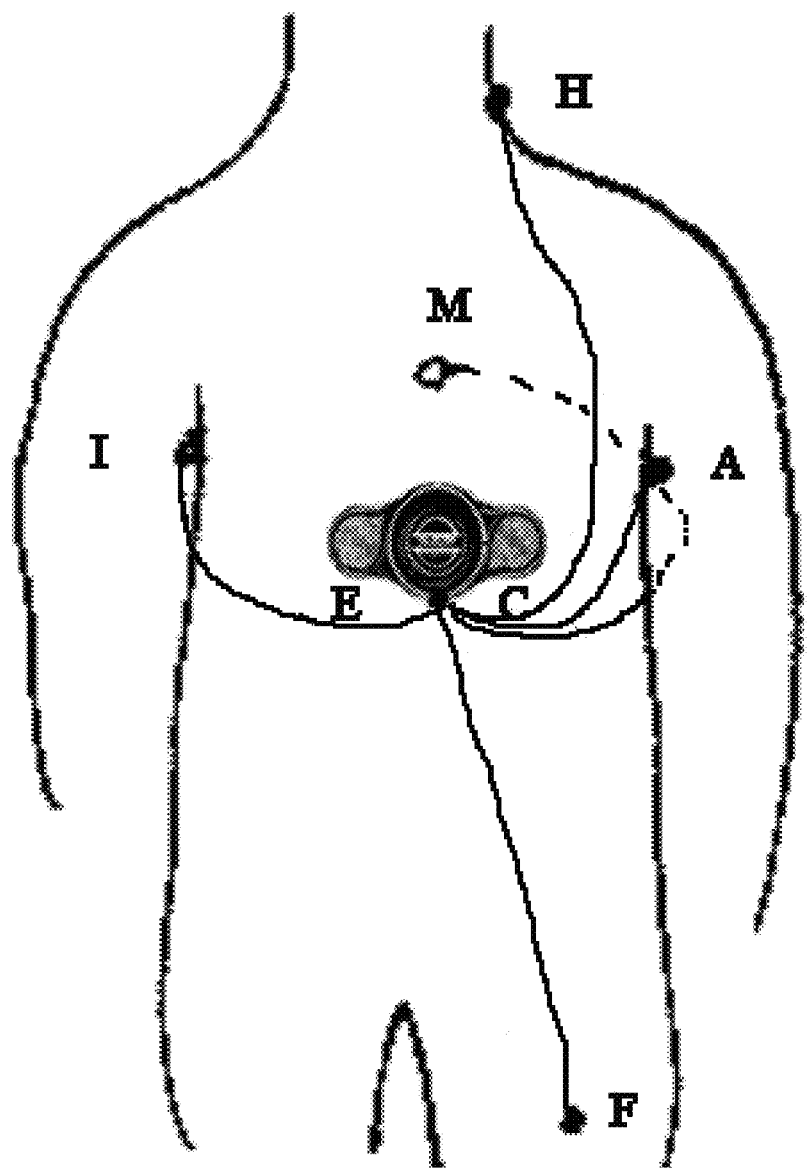
FIG. 22 is a schematic diagram of connections using frank leads according to Embodiment 8 of the present invention.

The two electrodes of the main body of the patch-type ECG acquisition equipment are adhered to the front side of the human body, and they are the electrodes E and C, and other extraction electrodes of the rear cover are adhered to corresponding positions. The electrodes A and C are combined to form an X lead together with I and a matched resistor, and a direction of axis X is from right to left. C, E and I are combined, while A and M are combined and matched with a resistor, which together form a Z lead, and a direction of axis Z is from back to front. M and F are combined, and form a Y lead together with H and a matched resistor, and a direction of axis Y is from top to bottom (as illustrated in FIG. 22). Of course, other multi-lead connections may also be designed for the user if necessary.

The above specific configurations can be easily understood by those skilled in the art.

The vibration motor of the preferred embodiment can send a vibration alarm when the battery electric quantity is low or the heart rate is abnormal according to the user's set on the matched mobile device.

The speaker of the preferred embodiment can send a sound alarm when the battery electric quantity is low or the heart rate is abnormal according to the user's set on the matched mobile device.

A surface of the main body of the patch-type ECG acquisition equipment of the preferred embodiment is further provided with an on/off button, and an on/off operation can be performed by pressing the button for a long duration.

The patch ECG acquisition equipment of the preferred embodiment is further provided with an emergency button, which can be pressed to send an emergency alarm to the system backend.

Figure 23:
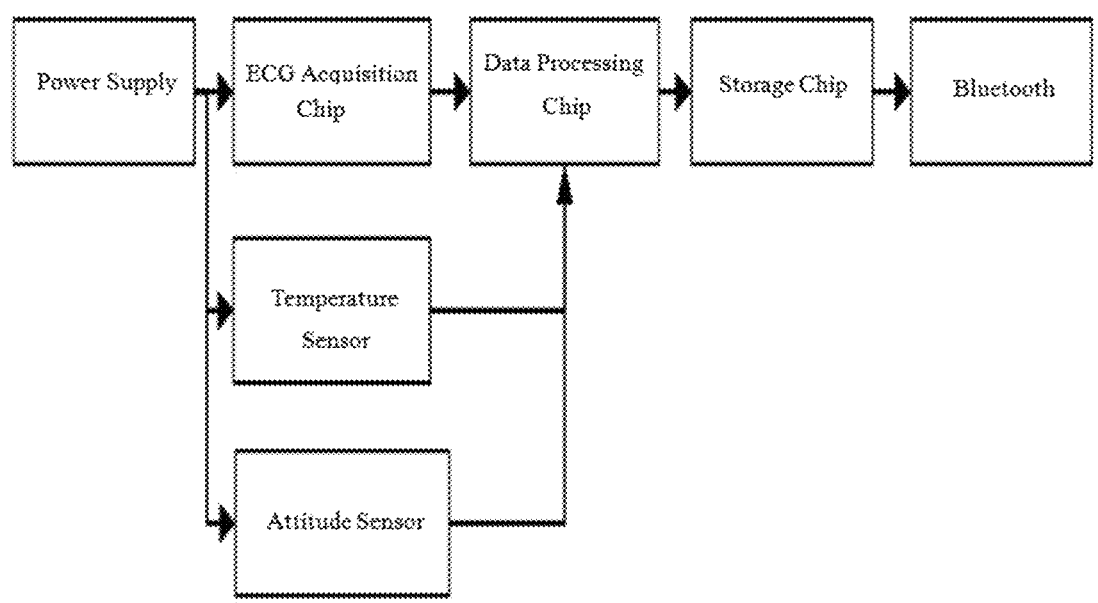
FIG. 23 is a schematic block diagram of a circuit module according to Embodiment 8 of the present invention.

FIG. 23 is a schematic block diagram of a circuit module of the patch-type ECG acquisition equipment, wherein a power supply is configured to supply power to the patch-type ECG acquisition equipment; an ECG acquisition chip is configured to acquire ECG data; a data processing chip is configured to process the acquired data, such as filtering, etc.; a storage chip is configured to store data; a Bluetooth module is configured to wirelessly transmit the processed data to a mobile device application for ECG signal analysis; a temperature sensor acquires a body temperature of a user so as to judge the physical condition of the user more comprehensively; and an attitude sensor is configured to acquire data to judge a motion state of the user.

When the patch-type ECG acquisition equipment of the preferred embodiment is used, the user firstly adheres the medical double-sided adhesive tape around the two electrode sheets, presses the on-off button for a long duration for startup, and adheres the patch-type ECG acquisition equipment to the user's skin in front of the heart so as to receive accurate ECG signals. The two electrode sheets form a loop with the human body and the circuit, and the ECG acquisition chip in the circuit module can acquire corresponding ECG signals (ECG data); the data processing chip filters the ECG data acquired by the ECG acquiring chip to filter out noise waves; finally, the filtered ECG data is stored in the storage chip. The user can choose two modes. One is to transmit the ECG data in the storage chip in real time to the terminal through the Bluetooth module for analyses, and the other is to transmit the ECG data to the cloud through the terminal for real-time analyses and receive the analyses results, or to copy complete ECG data from the external storage card for comprehensive data analysis after the whole acquisition process is completed.

Embodiment 9

In this embodiment, as compared with embodiment 8 and referring to FIG. 1, the first electrode and the second electrode each comprises an exposed part 11 and an embedded part 12, the exposed part 11 being exposed outside the front surface of the housing, and the embedded part 12 being packed in the housing by hard plastic portion. In this embodiment, the hard plastic is hard in texture and can generally refer to engineering plastic, such as ABS plastic, POM plastic, polycarbonate (PC), polyethylene terephthalate (PET), polybutylene terephthalate (PBT) and polyphenylene oxide (PPO). Some with harder texture can be medical-grade general-purpose plastic, such as polystyrene (PS). The front surface of the housing comprises a glue layer 4 provided with a contact surface hole corresponding to the exposed part in position, and the exposed part is provided with a positioning surface for quick adhesion with the glue layer; the bottom surface of the glue layer is adhered to a signal acquisition target, and the rear surface of the glue layer is adhered to the monitoring equipment; the contact surface hole comprises a first-type through-hole matched with an electrode of the monitoring equipment, and/or a second-type through-hole matched with a sensor of the monitoring equipment; the contact surface hole is matched with the electrode or the sensor at corresponding position in shape and size; in this embodiment, the glue layer is a double-sided adhesive tape composed of a medical double-sided adhesive tape; in some alternative embodiments of this embodiment, when the glue layer is a double-sided adhesive tape, the glue layer may be a non-woven double-sided adhesive tape; the glue layer may also be a flexible insulating material composed of nonpolar silica gel.

In order to improve the physiological signal acquisition capability of the contact surface layer, it is preferable to electroplate a silver/silver chloride film layer on the contact surface layer.

In order to facilitate the mounting of the contact surface layer, as illustrated in FIG. 6, the first electrode or the second electrode comprises a contact surface body 14 and a limiting flange 15 which are integrally formed, wherein the limiting flange 15 protrudes from an outer side wall of the contact surface body 14; meanwhile, the waterproof effect will be better by combining the contact surface body 14 and the limiting flange 15 with the hard plastic portion 24.

As illustrated in FIG. 6, only a front surface 142 of the contact surface body 14 is exposed after the encapsulation is completed, so the front surface 142 of the contact surface body 14 is the exposed part. The rest of the structure will be embedded into the housing, so the embedded part comprises the limiting flange 15 and portions of the contact surface body 14 except the front surface. The embedded part needs to be embedded with the hard plastic portion 24. At this time, the limiting flange 15 and the portions of the contact surface body 14 except the front surface 142 are embedded into the hard plastic portion 24, and a waterproof embedding surface is formed at a contact position with the hard plastic portion 24, because the limiting embedding surface is not one plane, but is formed by combining a plurality of planes or curved surfaces, i.e., the outer side wall surface 141 of the contact surface body 14, the front surface 151 of the limiting flange 15, the outer side wall surface 152 of the limiting flange 15 and the rear surface 153 of the limiting flange 15. Therefore, the formed boundary is tortuous, and it is more difficult for the liquid to enter the tortuous boundary. By utilizing the material characteristics of the hard plastic portion 24, the first electrode or the second electrode can have a good bonding with the hard plastic portion, thereby achieving a better waterproof effect with the aid of the tortuous boundary.

In some alternative embodiments of this embodiment, as illustrated in FIG. 7, the entire contact surface body 14 is exposed after the encapsulation is completed, so the contact surface body 14 is the exposed part. Correspondingly, the limiting flange 15 will be embedded into the encapsulation, so the embedded part comprises the limiting flange 15. The limiting flange 15 is embedded into the hard plastic portion 24 to form a waterproof embedding surface at the contact position with the hard plastic portion 24. The waterproof embedding surface is also not one plane, but is formed by combining a plurality of planes or curved surfaces, i.e., the front surface 151 of the limiting flange 15, the outer side wall surface 152 of the limiting flange 15 and the rear surface 153 of the limiting flange 15, so the boundary is also tortuous, and a better waterproof effect can be achieved.

Since the bonding surface of the hard plastic portion 24 and the embedded part is tortuous, the overall appearance of the hard plastic portion 24 is matched with the overall appearance of the embedded part correspondingly, so that the contact surface of the flexible silica gel and the hard plastic portion 24 can also be tortuous, thereby increasing the contact area between the flexible silica gel and the hard plastic portion 24 and improving the waterproof effect.

The first electrode and the second electrode are embedded into the hard plastic portion, and then the contact surface layer provided with the hard plastic portion is packaged, so that as compared with the existing first and second electrodes, the connection between the housing and the contact surface layer is tighter, the bonding is stronger, and the waterproofness is improved for the reason that the direct connection between the first and second electrodes and the flexible housing often cannot ensure a tight connection or bonding between the flexible housing and the first and second electrodes due to the difference in the respective characteristics of the materials; through the arrangement of the hard plastic portion, a connection bridge can be established between the flexible housing and the first and second electrodes, either the first and second electrodes or the flexible housing can have a strong bonding with the hard plastic portion, thereby solving the problem that the liquid can easily leak from the bonding surface due to the poor waterproof performance between the first and second electrodes and the housing. Through the above arrangement, the patch-type ECG acquisition equipment can reach a waterproof grade of IPX7, which is higher than living waterproof grade of an ordinary dry electrode.

As compared with the traditional electrocardiograph, electromyogram, electroencephalograph, etc., the physiological multi-parameter monitoring equipment has the following innovation points:

1. The equipment is integrated into a patch, is ultra-small, ultra-thin and ultra-light, can be directly adhered to a surface of a human body, can perform dynamic real-time acquisition of physiological parameter signals, is comfortable to wear for a long time, and can be used in exercises, shower, swimming and various life scenes;

2. The dry electrode is adopted and can be reused for many times. Through the above arrangement, the dry electrode can reach a waterproof grade of IPX7, which is higher than living waterproof grade of an ordinary dry electrode.

3. The reusable dry electrode is combined with the self-adhesive patch of the medical double-sided adhesive tape; one side is adhered to the soft silica gel of the main machine of the equipment, and the other side is adhered to the skin surface of the chest of the human body, so as to ensure the close fit between the equipment and the skin. Even if the human body moves frequently in an exercise state, the human engineering design can ensure the comfort and long-term wearing. The self-adhesive patch of the special medical double-sided adhesive tape ensures that the waterproof wearing will not fall off when the user is showering. The flexible silica gel and the self-adhesive patch of the double-sided adhesive tape adopted with the dry electrode, pass through strict biological compatibility tests, are made of medical-grade material, and thus are safer to be worn. At the same time, the ECG tips adopt the dry electrode and the self-adhesive patch of the medical double-sided adhesive tape to replace the traditional disposable button type wet electrode sheet, thus reducing the use cost for the users, realizing the goal of the long-term comfortable wearing and dynamic real-time monitoring of the ECG by the users, with a very important clinical application value.

From the traditional monitoring equipment to the personal or family monitoring equipment, the biggest change is not only to monitor in a static environment, but also to perform the parameter monitoring in an exercising state, in which the human body sweats a lot during wearing; on one hand, the equipment cannot be worn for a long time and is easy to fall off; on the other hand, the acquisition electrodes need to be reused for many times to meet the needs of personal long-term parameter monitoring. Finally, due to the need of repeated use for many times, the exposed dry electrode becomes the first choice, and the waterproof is a subsequent problem caused by the large amount of sweat and the exposed dry electrode.

The patch-type ECG acquisition equipment comprises a glue layer adhered to the front surface of the housing, also known as a self-adhesive patch, for the purpose of being firmly adhered to the human skin, especially when there is much sweat under the exercise conditions, thereby solving the problem of unreliable wearing in the prior art.

As illustrated in FIG. 8, the shape and size of the self-adhesive patch are consistent with those of the patch-type ECG acquisition equipment, comprising a non-woven double-sided adhesive tape 411, and two electrode through-holes 412 adhered to silica gel (not illustrated). The silica gel is matched with the contact surface hole in shape and size and it is aligned with the contact surface hole. The self-adhesive patch further comprises a sensor through-hole 413, which can be cooperated with a pulse wave sensor, a temperature sensor, etc. The two sides of the self-adhesive patch are respectively provided with gripping ears 414, which are non-adhesive and integrated with the non-woven double-sided adhesive tape 411, to facilitate the detachment of the non-adhesive film or release paper, or to tear off the self-adhesive patch from a signal acquisition target and/or signal acquisition equipment.

The shape and size of the self-adhesive patch are not limited to those illustrated in FIG. 8, and it may also be circular, square, rectangular, rhombus, etc. The self-adhesive patch may be matched with the signal acquisition equipment in shape and size, and its area may also be larger than that of the signal acquisition equipment.

In addition to the non-woven double-sided adhesive tape, a medical double-sided adhesive tape or nonpolar silica gel may also be used. The medical double-sided adhesive tape has a low production cost and a high safety, and it is advantageous for adhesion. When the nonpolar silica gel is removed from the skin, it will not cause damage to the fine hair and the skin and then reduce the pain.

The gripping ear may be disposed at any position around the self-adhesive patch, and is not limited to the two sides of the self-adhesive patch as illustrated in the drawings.

In the patch-type ECG acquisition equipment provided by this embodiment, a housing made of a flat flexible material and integrated with a pulse wave sensor is formed through a liquid silica gel injection molding or a solid silica gel compression molding, and a circuit module for processing the acquired physiological parameter data is sealed in the housing. According to the integrated design, the housing can be conveniently adhered to the human body through the medical double-sided adhesive tape, so that the wearing comfort and simplicity for the human body are improved, and the patch-type physiological multi-parameter monitoring equipment is also convenient to be worn and used. Meanwhile, it greatly improves the waterproof and sealing performance, and thoroughly solves the problem that the existing patch-type ECG acquisition equipment cannot be used during showering.

As illustrated in FIG. 9, the patch-type ECG acquisition equipment provided by this embodiment further comprising a black UV glue 415 and a miniature sucker array 416 disposed around a sensor contact surface hole 413; through the black UV glue, the light around an LED of the sensor can be shielded, thereby effectively avoiding the optical crosstalk between different LEDs, and improving the acquisition quality of signals such as pulse waves. The black UV glue has the advantages of high shading rate, strong adhesive force, quick UV curing speed and being suitable for the assembly line production. The miniature sucker array 416 can enhance the adhesion between the periphery of the through-hole and the skin; especially for a thin user, due to the influence of protruding ribs and sunken skin, ordinary suckers cannot be adsorbed on the skin surface; while the miniature sucker array can effectively overcome this problem due to the small sucker area and the large sucker number.

The sensor contact surface hole 413 may be used for not only acquisition of pulse waves, but also a skin characteristic sensor. The light emitting device of the skin characteristic sensor consists of three independent and non-interfering light sources, namely RGB white light, polarized light and ultraviolet light. The black UV glue functions to isolate the three light sources.

In addition to the black UV glue, any other glue or device capable of blocking light may also be disposed around the sensor contact surface hole.

As illustrated in FIG. 10, the self-adhesive patch comprises a non-woven double-sided adhesive tape 411, and two electrode contact surface holes (shielded by the silica gel). The silica gel is adhered to the electrode contact surface holes, protruded textures 417 are disposed on a surface of the silica gel, and a groove is formed between the adjacent textures.

The protruded textures increase the friction between the solid gel or the conductive silica gel and the skin, and also play an advantageous role for perspiration. Especially when the human body takes exercises, the grooves between the protruded textures will be full of sweat, which makes the adhesion between the solid gel or the conductive silica gel and the skin be tighter and firmer, and the sweat acts as a dielectric to improve the electrical conductivity. The conductivity rises as the sweat increases, and it is more suitable for use in exercises.

As the sweat will accumulate in the grooves between the textures 417, a large number of micropores can be disposed in the grooves and filled with hydrophilic porous media. When a sweat acquisition sensor is contacted with the textures 417, the sweat will be acquired by the sensor through the porous media with good water absorption.

FIG. 11 illustrates an exploded diagram of a self-adhesive patch, comprising a first-type release layer 421, a non-woven double-sided adhesive tape 411 including contact surface holes, and a second-type release layer 431 from top to bottom in sequence. The first-type release layer 421 is attached to a rear surface of the self-adhesive patch, i.e., the self-adhesive patch needs one side to be adhered to the acquisition equipment; the second-type release layer 431 is adhered to a bottom surface of the self-adhesive patch, i.e., the self-adhesive patch needs one side to be adhered to the human skin. The first-type release layer 421 is a segmented structure, and the segmentation is made between the contact surface holes of the self-adhesive patch, wherein 422 denotes an easily-torn line, and 423 denotes a gap line. When the patch is to be used, the left electrode contact surface hole is aligned with the electrode of the physiological multi-parameter acquisition equipment firstly, and after an accurate alignment, the segmented release layer on the left side of the easily-torn line is detached; next, the middle sensor contact surface hole is aligned with the sensor of the physiological multi-parameter acquisition equipment, and after an accurate alignment, the middle segmented release layer is detached; next, the right electrode contact surface hole is aligned with the electrode of the physiological multi-parameter acquisition equipment, and after an accurate alignment, the segmented release layer on the right side of the gap line is detached. The self-adhesive patch can be adhered to the acquisition equipment at one time by means of sequential alignments, and the contact surface holes are matched with the electrodes or the sensor, thereby avoiding the problem of repeated alignment. Finally, the second-type release layer 431 is detached and the self-adhesive patch can be adhered to the human skin.

One or more easily-torn lines or gap lines may be disposed on the segmented release layer, and between corresponding contact surface holes. The easily-torn line or the gap line may be disposed in segments between all of the contact surface holes so that each contact surface hole can be accurately aligned, or between some of the contact surface holes.

Similarly, in the case of a light exercise (non-strenuous exercise), the patch-type ECG acquisition equipment is adhered to the chest of the human body for ECG acquisition, and the comparative test results are as follows:

FIG. 12 illustrates ECG signals acquired by an ECG acquisition from a human body using an ECG acquisition equipment with a metal electrode, wherein the disposable self-adhesive patch as described above is not adhered to the metal electrode.

The skin will be stretched or contracted in the light exercise, while the metal has poor flexibility and self-adhesion, and the stretching performance is limited. Thus, the electrode is moved relative to the skin, rather than being tightly fitted with the skin, which will produce severely distorted ECG signals.

FIG. 13 illustrates ECG signals acquired by an ECG acquisition from a human body using an ECG acquisition equipment with a metal electrode, wherein a disposable self-adhesive patch is adhered to the metal electrode, a bottom surface of the electrode contact surface hole is hollow without a conductive medium adhered thereto.

As can be seen from the FIG. 13, the electrode is tightly fitted with the skin by the adhesion of the self-adhesive patch, and the quality of signal acquisition is improved. Except baseline drift and slight EMG noise, the signal waveform will not be distorted.

FIG. 14 illustrates ECG signals acquired by an ECG acquisition from a human body using an ECG acquisition equipment with an ordinary wet electrode, wherein the disposable self-adhesive patch as described above is not adhered to the ordinary wet electrode, and the ECG signal contains obvious EMG noise (burr).

Since the ordinary wet electrodes are two electrodes additionally led out from the ECG acquisition equipment and directly adhered to the human skin, they cannot be adhered to the patch, and there is no comparative test.

FIG. 15 illustrates ECG signals acquired by an ECG acquisition from a human body using an ECG acquisition equipment with a conductive silica gel electrode, wherein the disposable self-adhesive patch as described above is not adhered to the conductive silica gel electrode.

The waveforms with smaller amplitudes in the figure are the signals that should be acquired under normal conditions, while those with larger amplitudes are abnormal. There is almost no EMG noise in the signal, but the amplitude of the signal will change abruptly. This is because the conductive silica gel does not fit tightly with the skin when there is no other self-adhesive conductive medium.

FIG. 16 illustrates ECG signals acquired by an ECG acquisition from a human body using an ECG acquisition equipment with a conductive silica gel electrode, wherein a disposable self-adhesive patch is adhered to the conductive silica gel electrode, a conductive medium is adhered to the bottom surface of the electrode contact surface hole of the self-adhesive patch, and the conductive medium is solid gel or conductive silica gel. As compared with FIG. 15, the signals almost have no EMG noise or abnormal waveform, and the signal quality is significantly improved.

In a preferred embodiment, a self-adhesive patch as illustrated in FIG. 10 is adhered to the ECG acquisition equipment, and silica gel with textures is adhered to the electrode contact surface hole of the patch, and the ECG acquisition effect at this time is similar to that of FIG. 16.

In another preferred embodiment, a self-adhesive patch is adhered to the ECG acquisition equipment, and conductive silica gel with textures is adhered to the electrode contact surface hole of the patch; a liquid conductive medium is filled in the textures before the ECG signal acquisition, for example, mineral water is used to coat the conductive silica gel, and the ECG acquisition effect at this time is similar to that of FIG. 16.

In another preferred embodiment, a self-adhesive patch is adhered to the ECG acquisition equipment, and two layers of conductive media are adhered to the electrode contact surface hole of the patch, wherein one layer is conductive silica gel which is adhered to a double-sided adhesive tape; the other layer is silica gel, with one side adhered to the conductive silicon glue layer, and the other side in contact with human skin. The ECG acquisition effect at this time is similar to FIG. 16.

Through the comparisons between FIG. 12 and FIGS. 13, 15 and 16, it can be seen that the signal acquired after adding the self-adhesive patch is obviously better than the previous signal.

The electrical properties of the wet electrode and the conductive silica gel are tested and compared according to a Chinese medicine industry standard YY/T 0196-2005 Disposable ECG Electrodes. The experimental results are listed below. It can be seen that the electrical properties of conductive silica gel are significantly better than those of the ordinary wet electrode, thus explaining to some extent that the signal acquisition effect of the self-adhesive patch using solid gel and conductive silica gel is significantly better than that of the ordinary wet electrode. From the above comparison, it can be seen that the EMG noise in the signal of FIG. 16 is basically eliminated.

| Test item | Category | | | Result comparison |
| --- | --- | --- | --- | --- |
| | Wet electrode | Conductive silica gel | Criterion | |
| AC impedance | The resistance value changes rapidly. In about 4 minutes, the resistance value decreases from 403.2 ohms to 359 ohms, and then increases rapidly to 404.2 ohms | The resistance value changes slowly, decreasing from 63.4 ohms to 56.9 ohms within the observation time (1 hour) | The average impedance does not exceed 2 KΩ, and the impedance of individual glue-to-glue electrode does not exceed 3 KΩ | The AC impedance of the conductive silica gel glue-to-glue electrode is smaller than that of the wet electrode |
| DC offset voltage | 94.8 mV | 0.1 mV | After a one-minute stable period, the offset voltage is not more than 100 mV | The DC offset voltage of the conductive silica gel is significantly lower than that of the wet electrode |
| Bias current tolerance | From −49.8 mV, the negative voltage decreases to 0 at a change rate of about 0.1 mV/s, and then the positive voltage increases at a rate of 0.005 mV/s; after increasing to 11.2 mV, the voltage changes again to be negative and the change rate gradually decreases. | The voltage is always kept at 0 mV without any change. | 200 nA direct current is applied, the observed voltage variation across the electrode pair over the entire duration is not more than 100 mV. | The bias current tolerance of the conductive silica gel is better than that of the wet electrode |

Those skilled in the art will appreciate that it is possible to make many modifications to the above description, so the embodiments and the drawings are only used to describe one or more specific embodiments.

Although the exemplary embodiments deemed as the present invention have been described and illustrated, it will be apparent to those skilled in the art that various changes and substitutions can be made thereto without departing from the spirit of the present invention. In addition, many modifications can be made to adapt particular situations to the teachings of the present invention without departing from the central concept of the present invention described herein. Therefore, the present invention is not limited to the specific embodiments disclosed herein, but may also include all embodiments falling within the scope of the present invention and their equivalents.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A non-disposable/reusable dry electrode, comprising an encapsulation, extraction electrode and a contact surface layer, wherein the extraction electrode and the contact surface layer are disposed in the encapsulation; the encapsulation comprises a first surface and a second surface, the extraction electrode being exposed on the second surface and connected with the contact surface layer, and a glue layer being disposed on the first surface; the contact surface layer comprises an exposed part and an embedded part, the embedded part being disposed in the encapsulation, and the exposed part being exposed on the first surface; the glue layer is provided with an contact surface hole corresponding to the exposed part in position; and the exposed part is provided with a positioning surface for quick adhesion with the glue layer; preferably, a material of the contact surface layer is conductive silica gel; further preferably, a surface of the exposed part of the contact surface layer is provided with protruded textures, and a groove is formed between the adjacent textures, preferably, conductive filling materials of the conductive silica gel are nickel-coated copper powder and conductive graphite; preferably, the encapsulation is configured to be a flexible insulating encapsulation;
preferably, the extraction electrode is selected from one of the followings: a metal joint vertically disposed on the second surface, an outgoing wire horizontally disposed on the second surface, and an electrode interface horizontally disposed on the second surface.

2. A waterproof dry electrode, comprising an encapsulation, extraction electrode and a contact surface layer, wherein the extraction electrode and the contact surface layer are connected with each other and disposed in the encapsulation; the contact surface layer comprises an exposed part and an embedded part, the exposed part being exposed outside the encapsulation; the encapsulation comprises flexible silica gel and hard plastic portion, the embedded part being embedded into the hard plastic portion, and the hard plastic portion being packaged in the flexible silica gel;
wherein the contact surface layer comprises a contact surface body and a limiting flange which are integrally formed, the limiting flange protruding from an outer side wall of the contact surface body;
preferably, a front surface of the contact surface body is the exposed part; the embedded part comprises the limiting flange and portions of the contact surface body except the front surface; the limiting flange and the portions of the contact surface body except the front surface are embedded into the hard plastic portion, and a waterproof embedding surface is formed at a contact position with the hard plastic portion;
preferably, the contact surface body is the exposed part, and the embedded part comprises the limiting flange; the limiting flange is embedded into the hard plastic portion, and a waterproof embedding surface is formed at a contact position with the hard plastic portion.

3. The waterproof dry electrode according to claim 2, wherein preferably, an overall appearance of the hard plastic portion is matched with an overall appearance of the embedded part to increase a contact area between the flexible silica gel and the hard plastic portion;
preferably, the material of the contact surface layer is a conductive material;
preferably, a silver/silver chloride film layer is electroplated on the contact surface layer; more preferably, a surface of the exposed part of the contact surface layer is provided with protruded textures, and a groove is formed between the adjacent textures;
preferably, a material of the contact surface layer is conductive silica gel; more preferably, conductive filling materials of the conductive silica gel are nickel-coated copper powder and conductive graphite;
preferably, the material of the contact surface layer is metal, and the silver/silver chloride film layer is electroplated on the metal; more preferably, a portion of the extraction electrode located in the encapsulation is connected with the embedded part of the contact surface layer by riveting, butt-welding, laser spot welding or soldering.

4. The waterproof dry electrode according to claim 2, wherein the encapsulation comprises a first surface and a second surface, the extraction electrode being exposed on the second surface, a glue layer being disposed on the first surface, and the exposed part being exposed on the first surface; the glue layer is provided with an contact surface hole corresponding to the exposed part in position; and the exposed part is provided with a positioning surface for quick adhesion with the glue layer;
preferably, the extraction electrode is a metal joint vertically disposed on the second surface, or an outgoing wire horizontally disposed on the second surface, or an electrode interface horizontally disposed on the second surface, or an electrode interface horizontally or vertically disposed on the first surface;
preferably, the glue layer comprises a double-sided adhesive tape or a flexible insulating material; the double-sided adhesive tape comprises a medical double-sided adhesive tape or a non-woven double-sided adhesive tape, and the flexible insulating material comprises nonpolar silica gel;
preferably, a shape and a size of the contact surface hole are matched with those of an electrode or a sensor of a signal acquisition equipment;
preferably, light shading glue and/or a miniature sucker array is disposed around the contact surface hole on a bottom surface of the glue layer;
preferably, a rear surface of the glue layer is covered with a first-type release layer, and/or the bottom surface of the glue layer is covered with a second-type release layer; the first-type release layer is a segmented release layer, an easily-torn line and/or a gap line being disposed between the contact surface holes for segmentation;
more preferably, edges of the glue layer are provided with gripping ears that are integrated with the glue layer, and the gripping ears are non-adhesive to facilitate detachment of the first-type release layer and the second-type release layer, or to tear off the glue layer from a signal acquisition target and/or the dry electrode;

further preferably, the bottom surface of the glue layer is covered with a conductive medium matched with the contact surface hole in shape and size, the conductive medium being aligned with the contact surface hole and adhered to the glue layer;

preferably, the conductive medium comprises solid gel, a metal sheet or conductive silica gel, wherein the solid gel comprises silica gel; more preferably, a surface of the solid gel or the conductive silica gel is provided with protruded textures, and a groove is formed between the adjacent textures.

5. A physiological multi-parameter monitoring equipment, comprising a circuit module, a flexible housing, a first electrode and a second electrode, wherein the circuit module is packaged in the housing; the first electrode and the second electrode are exposed on a front surface of the housing to acquire electrocardiogram (ECG) signals, electromyogram (EMG) signals or electroencephalogram (EEG) signals and are connected with the circuit module by wires; the first electrode and the second electrode are the dry electrodes according to claim 1;

preferably, further comprising an upper cover detachably and sealably mounted on a rear surface of the housing, wherein a battery is disposed in the upper cover, and electrically connected with the circuit module in the housing through the upper cover and correspondingly disposed metal contacts on the housing; and the battery can be taken out from the upper cover for replacement or is a rechargeable battery; further preferably, the upper cover is mounted in a groove disposed on the rear surface of the housing, and the fastened upper cover is tightly pressed on a flexible material of the housing to achieve waterproofness; preferably, the upper cover is screwed into a circular groove disposed at the rear surface of the housing by means of thread matching;

preferably, the front surface of the housing is provided with a double-sided adhesive material having a through-hole, wherein a bottom surface of the double-sided adhesive material can be adhered to a signal acquisition target, a rear surface of the double-sided adhesive material is adhered to the monitoring equipment, and the signal acquisition target is adhered to a signal acquisition equipment through the double-sided adhesive material; the through-hole comprises a first-type through-hole matched with an electrode of the signal acquisition equipment, and/or a second-type through-hole matched with a sensor of the signal acquisition equipment; further preferably, the double-sided adhesive material comprises a double-sided adhesive tape or a flexible insulating material, wherein the double-sided adhesive tape comprises a medical double-sided adhesive tape or a non-woven double-sided adhesive tape, and the flexible insulating material comprises nonpolar silica gel; the through-hole is matched with the electrode or the sensor of the signal acquisition equipment in shape and size; the bottom surface of the double-sided adhesive material is covered with a conductive medium matched with the first-type through-hole in shape and size, wherein the conductive medium is aligned with the first-type through-hole and adhered to the double-sided adhesive material;

preferably, the conductive medium comprises solid gel, a metal sheet or conductive silica gel, and the solid gel comprises silica gel; a surface of the solid gel or the conductive silica gel is provided with protruded textures, and a groove is formed between the adjacent textures; light shading glue and/or a miniature sucker array is disposed around the second-type through-hole on the bottom surface of the double-sided adhesive material;

the rear surface of the double-sided adhesive material is covered with a first-type release layer, and/or the bottom surface of the double-sided adhesive material is covered with a second-type release layer; the first-type release layer is a segmented release layer, an easily-torn line and/or a gap line being disposed between the through-holes for segmentation; further preferably, edges of the double-sided adhesive material are provided with gripping ears that are integrated with the double-sided adhesive material, and the gripping ears are non-adhesive to facilitate detachment of the first-type release layer and the second-type release layer, or to tear off a self-adhesive patch from the signal acquisition target and/or the monitoring equipment.

6. The physiological multi-parameter monitoring equipment according to claim 5, which is a patch-type ECG acquisition equipment, comprising the housing made of a flat flexible material suitable for being adhered to a human skin, and a front surface of the housing is provided with the first electrode and the second electrode for acquiring ECG signals by being adhered to the human skin; the housing is integrally formed with the first electrode and the second electrode through a liquid silica gel injection molding or a solid silica gel compression molding; the circuit module for processing acquired ECG data is sealed in the housing, and is connected with the first electrode and the second electrode.

7. The physiological multi-parameter monitoring equipment according to claim 6, further comprising:

an upper cover detachably and sealably mounted on a rear surface of the housing, wherein a battery is disposed in the upper cover, and electrically connected with the circuit module in the housing through the upper cover and correspondingly disposed metal contacts on the housing; and the battery can be taken out from the upper cover for replacement or is a rechargeable battery;

preferably, the upper cover is mounted in a groove disposed on the rear surface of the housing, and the fastened upper cover is tightly pressed on a flexible material of the housing to achieve waterproofness; preferably, the upper cover is screwed into a circular groove disposed at the rear surface of the housing by means of thread matching;

preferably, a surface of the housing covered by the upper cover is provided with an external storage card slot for inserting an external storage card, and the external storage card slot is connected with the circuit module to store ECG data acquired and processed by the circuit module into the external storage card;

preferably, the upper cover is located at a middle portion of the housing, the first electrode and the second electrode are located at two sides of the upper cover, respectively, and preferably the housing has a circular arc-shape, which is wide at the middle portion, and gradually narrowed towards two sides.

8. The physiological multi-parameter monitoring equipment according to claim 6, further comprising:

other electrodes configured to acquire ECG signals, the other electrodes being led out from the upper cover or the housing through lead wires and electrically connected with the circuit module in the housing through the upper cover and correspondingly disposed metal contacts on the housing; and the other electrodes can form various ECG lead system together with the first electrode and the second electrode;

preferably, a temperature sensor is disposed on the front surface of the housing, the housing being integrally formed with the temperature sensor through a liquid silica gel injection molding or a solid silica gel compression molding; the temperature sensor comprises a contact type temperature sensor and a non-contact type temperature sensor to acquire a body temperature and an ambient temperature, and transmit acquired body temperature information to the circuit module; and/or the contact type temperature sensor is multiplexed into a third electrode for detecting whether leads fall off during ECG or EEG monitoring; the non-contact temperature sensor is preferably an infrared temperature sensor; and/or an attitude sensor disposed in the housing and configured to acquire motion and direction data to judge a motion state of a user; preferably, the attitude sensor is a three-axis sensor, a six-axis sensor or a nine-axis sensor;

preferably, further comprising a near-infrared light sensor disposed on the front surface and/or the back surface of the housing, the housing being integrally formed with the near-infrared light sensor through a liquid silica gel injection molding or a solid silica gel compression molding; the circuit module is connected with the near-infrared light sensor which is configured for a non-invasive detection of a blood oxygen saturation, a blood pressure and a blood glucose of a human body;

preferably, further comprising a skin sensor disposed on the front surface of the housing, the housing being integrally formed with the skin sensor through a liquid silica gel injection molding or a solid silica gel compression molding; the skin sensor is configured to acquire skin information of a user and transmit the acquired skin information to the circuit module;

preferably, further comprising a sweat sensor disposed on the front surface of the housing, the housing being integrally formed with the sweat sensor through a liquid silica gel injection molding or a solid silica gel compression molding; the sweat sensor is configured to acquire respective physiological parameter data of sweat of a user and transmit the acquired physiological parameter data to the circuit module;

preferably, further comprising an environmental detector disposed on the housing, the housing being integrally formed with the environmental detector through a liquid silica gel injection molding or a solid silica gel compression molding; the environmental detector comprises a temperature and humidity sensor, an atmospheric pressure sensor, an optical sensor and an optical air quality sensor, and is configured to detect environmental parameters and transmit environmental parameter data to the circuit module;

preferably, further comprising a wireless communication module disposed in the housing, wherein the wireless communication module is configured to wirelessly transmit the ECG data processed by the circuit module to a terminal;

preferably, further comprising an alarm device, which is connected with the circuit module and configured to generate an emergency alarm in case of emergency by a manual operation or automatically generate an alarm under set conditions, wherein the set conditions include that the circuit module detects a battery low electric quantity, an abnormal heart rhythm, an abnormal EEG or other abnormal parameters;

preferably, the alarm device comprises a button and a vibration motor or a speaker or a diode lamp for flashing alarm.

9. The physiological multi-parameter monitoring equipment according to claim 6, wherein the first electrode and the second electrode each comprises an exposed part and an embedded part, the exposed part being exposed outside the front surface of the housing, and the embedded part being packed in the housing by hard plastic portion;

preferably, an overall appearance of the hard plastic portion is matched with an overall appearance of the embedded part to increase a contact area between the flexible silica gel and the hard plastic portion;

preferably, a silver/silver chloride film layer is electroplated on the first electrode and the second electrode.

10. The physiological multi-parameter monitoring equipment according to claim 9, wherein the first electrode or the second electrode comprises a contact surface body and a limiting flange which are integrally formed, the limiting flange protruding from an outer side wall of the contact surface body;

preferably, a front surface of the contact surface body is the exposed part; the embedded part comprises the limiting flange and portions of the contact surface body except the front surface; the limiting flange and the portions of the contact surface body except the front surface are embedded into the hard plastic portion, and a waterproof embedding surface is formed at a contact position with the hard plastic portion;

preferably, the contact surface body is the exposed part, and the embedded part comprises the limiting flange; the limiting flange is embedded into the hard plastic portion, and a waterproof embedding surface is formed at a contact position with the hard plastic portion.

11. The physiological multi-parameter monitoring equipment according to claim 9, wherein the front surface of the housing comprises a glue layer provided with a contact surface hole corresponding to the exposed part in position, and the exposed part is provided with a positioning surface for quick adhesion with the glue layer;

preferably, the contact surface hole comprises a first-type through-hole matched with the first electrode or the second electrode of the ECG acquisition equipment, and/or a second-type through-hole matched with a sensor of the ECG acquisition equipment;

preferably, the glue layer comprises a double-sided adhesive tape or a flexible insulating material; the double-sided adhesive tape comprises a medical double-sided adhesive tape or a non-woven double-sided adhesive tape, and the flexible insulating material comprises nonpolar silica gel;

preferably, the contact surface hole is matched with the electrode or the sensor of the signal acquisition equipment in shape and size.

12. The physiological multi-parameter monitoring equipment according to claim 11, wherein a bottom surface of the glue layer is covered with a conductive medium matched with the first-type through-hole in shape and size, and the conductive medium is aligned with the first-type through-hole and adhered to the glue layer;

preferably, the conductive medium comprises solid gel, a metal sheet or conductive silica gel, or ECG coupling agent, and the solid gel comprises silica gel; further preferably, a surface of the solid gel or the conductive silica gel is provided with protruded textures, and a groove is formed between the adjacent textures;

preferably, light shading glue and/or a miniature sucker array is disposed around the second-type through-hole on the bottom surface of the glue layer;

preferably, a rear surface of the glue layer is covered with a first-type release layer, and/or the bottom surface of the glue layer is covered with a second-type release layer; the first-type release layer is a segmented release layer, an easily-torn line and/or a gap line being disposed between the contact surface holes for segmentation;

further preferably, edges of the glue layer are provided with gripping ears that are integrated with the glue layer, and the gripping ears are non-adhesive to facilitate detachment of the first-type release layer and the second-type release layer, or to tear off the glue layer from a signal acquisition target and/or acquisition equipment.

13. A physiological multi-parameter monitoring equipment, comprising a circuit module, a flexible housing, a first electrode and a second electrode, wherein the circuit module is packaged in the housing; the first electrode and the second electrode are exposed on a front surface of the housing to acquire electrocardiogram (ECG) signals, electromyogram (EMG) signals or electroencephalogram (EEG) signals and are connected with the circuit module by wires; the first electrode and the second electrode are the dry electrodes according to claim 2;

preferably, further comprising an upper cover detachably and sealably mounted on a rear surface of the housing, wherein a battery is disposed in the upper cover, and electrically connected with the circuit module in the housing through the upper cover and correspondingly disposed metal contacts on the housing; and the battery can be taken out from the upper cover for replacement or can be a rechargeable battery;

further preferably, the upper cover is mounted in a groove disposed on the rear surface of the housing, and the fastened upper cover is tightly pressed on a flexible material of the housing to achieve waterproofness; preferably, the upper cover is screwed into a circular groove disposed at the rear surface of the housing by means of thread matching;

preferably, the front surface of the housing is provided with a double-sided adhesive material having through-holes, wherein a bottom surface of the double-sided adhesive material can be adhered to a signal acquisition target, a rear surface of the double-sided adhesive material is adhered to the monitoring equipment, and the signal acquisition target is adhered to a signal acquisition equipment through the double-sided adhesive material; the through-hole comprises a first-type through-hole matched with an electrode of the signal acquisition equipment, and/or a second-type through-hole matched with a sensor of the signal acquisition equipment; further preferably, the double-sided adhesive material comprises a double-sided adhesive tape or a flexible insulating material, wherein the double-sided adhesive tape comprises a medical double-sided adhesive tape or a non-woven double-sided adhesive tape, and the flexible insulating material comprises nonpolar silica gel; the through-hole is matched with the electrode or the sensor of the signal acquisition equipment in shape and size; the bottom surface of the double-sided adhesive material is covered with a conductive medium matched with the first-type through-hole in shape and size, wherein the conductive medium is aligned with the first-type through-hole and adhered to the double-sided adhesive material;

preferably, the conductive medium comprises solid gel, a metal sheet or conductive silica gel, and the solid gel comprises silica gel; a surface of the solid gel or the conductive silica gel is provided with protruded textures, and a groove is formed between the adjacent textures; light shading glue and/or a miniature sucker array is disposed around the second-type through-hole on the bottom surface of the double-sided adhesive material; the rear surface of the double-sided adhesive material is covered with a first-type release layer, and/or the bottom surface of the double-sided adhesive material is covered with a second-type release layer; the first-type release layer is a segmented release layer, an easily-torn line and/or a gap line being disposed between the through-holes for segmentation; further preferably, edges of the double-sided adhesive material are provided with gripping ears that are integrated with the double-sided adhesive material, and the gripping ears are non-adhesive to facilitate detachment of the first-type release layer and the second-type release layer, or to tear off a self-adhesive patch from the signal acquisition target and/or the monitoring equipment.

14. The physiological multi-parameter monitoring equipment according to claim 13, which is a patch-type ECG acquisition equipment, comprising the housing made of a flat flexible material suitable for being adhered to a human skin, and a front surface of the housing is provided with the first electrode and the second electrode for acquiring ECG signals by being adhered to the human skin; the housing is integrally formed with the first electrode and the second electrode through a liquid silica gel injection molding or a solid silica gel compression molding; the circuit module for processing acquired ECG data is sealed in the housing, and is connected with the first electrode and the second electrode.

15. The physiological multi-parameter monitoring equipment according to claim 14, further comprising:

an upper cover detachably and sealably mounted on a rear surface of the housing, wherein a battery is disposed in the upper cover, and electrically connected with the circuit module in the housing through the upper cover and correspondingly disposed metal contacts on the housing; and the battery can be taken out from the upper cover for replacement or is a rechargeable battery;

preferably, the upper cover is mounted in a groove disposed on the rear surface of the housing, and the fastened upper cover is tightly pressed on a flexible material of the housing to achieve waterproofness; preferably, the upper cover is screwed into a circular groove disposed at the rear surface of the housing by means of thread matching;

preferably, a surface of the housing covered by the upper cover is provided with an external storage card slot for inserting an external storage card, and the external storage card slot is connected with the circuit module to store ECG data acquired and processed by the circuit module into the external storage card;

preferably, the upper cover is located at a middle portion of the housing, the first electrode and the second electrode are located at two sides of the upper cover, respectively, and preferably the housing has a circular arc-shape, which is wide at the middle portion, and gradually narrowed towards two sides.

16. The physiological multi-parameter monitoring equipment according to claim 14, further comprising:
a temperature sensor disposed on the front surface of the housing, wherein the housing is integrally formed with the temperature sensor through a liquid silica gel injection molding or a solid silica gel compression molding, and the temperature sensor is configured to detect a body temperature and transmit acquired body temperature information to the circuit module; and/or an attitude sensor disposed in the housing and configured to acquire motion and direction data to judge a motion state of a user; preferably, the attitude sensor is a three-axis sensor, a six-axis sensor or a nine-axis sensor;
preferably, further comprising a wireless communication module disposed in the housing, wherein the wireless communication module is configured to wirelessly transmit the ECG data processed by the circuit module to a terminal;
preferably, further comprising an alarm device, which is connected with the circuit module and configured to generate an alarm under set conditions, wherein the set conditions include that the circuit module detects a low battery level or an abnormal heart rhythm; preferably, the alarm device is a vibration motor or a speaker;
preferably, further comprising other electrodes configured to acquire ECG signals, the other electrodes being led out from the upper cover or the housing through lead wires and electrically connected with the circuit module in the housing through the upper cover and correspondingly disposed metal contacts on the housing; and the other electrodes can form various lead forms together the first electrode and the second electrode.

17. The physiological multi-parameter monitoring equipment according to claim 14, wherein the first electrode and the second electrode each comprises an exposed part and an embedded part, the exposed part being exposed outside the front surface of the housing, and the embedded part being packed in the housing by hard plastic portion;
preferably, an overall appearance of the hard plastic portion is matched with an overall appearance of the embedded part to increase a contact area between the flexible silica gel and the hard plastic portion;
preferably, a silver/silver chloride film layer is electroplated on the first electrode and the second electrode.

18. The physiological multi-parameter monitoring equipment according to claim 17, wherein the first electrode or the second electrode comprises a contact surface body and a limiting flange which are integrally formed, the limiting flange protruding from an outer side wall of the contact surface body;
preferably, a front surface of the contact surface body is the exposed part; the embedded part comprises the limiting flange and portions of the contact surface body except the front surface; the limiting flange and the portions of the contact surface body except the front surface are embedded into the hard plastic portion, and a waterproof embedding surface is formed at a contact position with the hard plastic portion;
preferably, the contact surface body is the exposed part, and the embedded part comprises the limiting flange; the limiting flange is embedded into the hard plastic portion, and a waterproof embedding surface is formed at a contact position with the hard plastic portion.

19. The physiological multi-parameter monitoring equipment according to claim 17, wherein the front surface of the housing comprises a glue layer provided with a contact surface hole corresponding to the exposed part in position, and the exposed part is provided with a positioning surface for quick adhesion with the glue layer;
preferably, the contact surface hole comprises a first-type through-hole matched with the first electrode or the second electrode of the ECG acquisition equipment, and/or a second-type through-hole matched with a sensor of the ECG acquisition equipment;
preferably, the glue layer comprises a double-sided adhesive tape or a flexible insulating material; the double-sided adhesive tape comprises a medical double-sided adhesive tape or a non-woven double-sided adhesive tape, and the flexible insulating material comprises nonpolar silica gel;
preferably, the contact surface hole is matched with the electrode or the sensor of the signal acquisition equipment in shape and size;
further preferably, a bottom surface of the glue layer is covered with a conductive medium matched with the first-type through-hole in shape and size, and the conductive medium is aligned with the first-type through-hole and adhered to the glue layer;
preferably, the conductive medium comprises solid gel, a metal sheet or conductive silica gel, and the solid gel comprises silica gel; further preferably, a surface of the solid gel or the conductive silica gel is provided with protruded textures, and a groove is formed between the adjacent textures;
preferably, light shading glue and/or a miniature sucker array is disposed around the second-type through-hole on the bottom surface of the glue layer;
preferably, a rear surface of the glue layer is covered with a first-type release layer, and/or the bottom surface of the glue layer is covered with a second-type release layer; the first-type release layer is a segmented release layer, an easily-torn line and/or a gap line being disposed between the contact surface holes for segmentation;
further preferably, edges of the glue layer are provided with gripping ears that are integrated with the glue layer, and the gripping ears are non-adhesive to facilitate detachment of the first-type release layer and the second-type release layer, or to tear off the glue layer from a signal acquisition target and/or acquisition equipment.

* * * * *